(12) United States Patent
Heudré et al.

(10) Patent No.: US 10,219,522 B2
(45) Date of Patent: Mar. 5, 2019

(54) ANTIMICROBIAL COMPOSITIONS

(71) Applicant: NATUREX S.A., Avignon (FR)

(72) Inventors: Mélanie Marie-Paule Patricia Heudré, Vedene (FR); Simona Birtic, Cavaillon (FR); François-Xavier Henri Pierre, Jonquerettes (FR); Xavier Pierre François Mesnier, Lausanne (CH); Anne Passemard, Entraigues-sur-la-Sorgue (FR); Antoine Charles Bily, Vedene (FR); Marc Roller, Morieres les Avignon (FR)

(73) Assignee: NATUREX S.A., Avignon (FR)

( * ) Notice: Subject to any disclaimer, the term of this patent is extended or adjusted under 35 U.S.C. 154(b) by 340 days.

(21) Appl. No.: 14/615,968

(22) Filed: Feb. 6, 2015

(65) Prior Publication Data

US 2016/0227799 A1    Aug. 11, 2016

(51) Int. Cl.
| | |
|---|---|
| *A23B 4/20* | (2006.01) |
| *A23B 4/22* | (2006.01) |
| *A23L 3/3472* | (2006.01) |
| *A23L 3/349* | (2006.01) |
| *A23L 3/3508* | (2006.01) |
| *A61K 36/00* | (2006.01) |

(52) U.S. Cl.
CPC .................. *A23B 4/20* (2013.01); *A23B 4/22* (2013.01); *A23L 3/349* (2013.01); *A23L 3/3472* (2013.01); *A23L 3/3508* (2013.01); *A23V 2002/00* (2013.01); *A61K 36/00* (2013.01); *Y02A 40/944* (2018.01)

(58) Field of Classification Search
CPC . A23B 4/20; A23B 4/22; A23L 3/3472; A23L 3/349; A23L 3/3508; A23V 2002/00; A61K 36/00; Y02A 40/944
USPC ....... 426/321, 324, 331, 332, 335, 532, 654, 426/655
See application file for complete search history.

(56) References Cited

U.S. PATENT DOCUMENTS

| | | | | |
|---|---|---|---|---|
| 6,352,712 | B1* | 3/2002 | Lukaczer | A23L 33/16 424/439 |
| 7,790,205 | B2* | 9/2010 | Tripp | A61K 31/12 424/725 |
| 2004/0131709 | A1 | 7/2004 | Berdahl | |
| 2010/0159085 | A1 | 6/2010 | Sandusky | |
| 2014/0242198 | A1 | 8/2014 | Modak | |

FOREIGN PATENT DOCUMENTS

| | | |
|---|---|---|
| CN | 102 599 612 | 7/2012 |
| WO | WO-2012/028928 | 3/2012 |

OTHER PUBLICATIONS

Fernandes-Lopez, et al., "Antioxidant and antibacterial activities of natural extracts: application in beef meatballs", Mar. 1, 2005, pp. 371-380, vol. 69, No. 3, XP027770765, Meat Science, Elsevier Science, GB.*
Ahn, et al., "Effects of plant extracts on microbial growth, color change, and lipid oxidation in cooked beef", Feb. 1, 2007, pp. 7-14, vol. 24, No. 1, Food Microbiology, Academic Press, Ltd., London, GB.
Negi, P. S., et al., "Antioxidant and Antibacterial Activities of Punica Granatum Peel Extracts", May 1, 2003, pp. 1473-1477, vol. 68, No. 4, Journal of Food Science, Wiley-Blackwell Publishing, Inc., US.
International Search Report dated Jun. 2, 2016 in corresponding International Patent Application No. PCT/IB2016/000178.
Written Opinion dated Jun. 2, 2016 in corresponding International Patent Application No. PCT/IB2016/000178.

* cited by examiner

*Primary Examiner* — Leslie A Wong
(74) *Attorney, Agent, or Firm* — Stephen J. Weyer, Esq.; Stites & Harbison, PLLC

(57) ABSTRACT

A composition includes *Punica* extract and a Lamiaceae extract, wherein a majority of the volatile oil components have been removed from the Lamiaceae extract. A method for applying the composition to a food which includes but is not limited to fresh/unprocessed and processed meat, fish or poultry is also provided.

31 Claims, 11 Drawing Sheets

ANTIMICROBIAL COMPOSITIONS

FIELD OF THE INVENTION

The present invention relates to compositions for extending color and/or microbial stability to food and in particular to compositions which extend color and/or microbial stability to food, including, but not limited to meat, fish or poultry (fresh/unprocessed and processed). These compositions that are effective in extending the color and microbiological stability of food.

BACKGROUND OF THE INVENTION

Food safety and prevention of food spoilage is an ever present concern worldwide, particularly within the meat industry. Spoilage of food is a major economic problem for a food manufacturer. Food manufacturers need to protect the health and safety of the public by delivering products that are safe to eat. Such food must have a guaranteed shelf life, either at chilled or ambient temperature storage. Consumers prefer good tasting food of high quality. This is difficult to achieve with chemical preservatives, harsh heating regimes and other processing measures. Food safety and protection is best achieved with a multiple preservation system using a combined approach of milder processing and natural preservatives. Foodborne micro-organisms are also less able to adapt and grow in food preserved with different preservative measures.

There is much concern about food protection and the growth of food spoilage organisms such as *Listeria monocytogenes*. This particular species is one of the most problematic spoilage microorganism in meat. The unusual physiological characteristics such as exceptional resistance toward antimicrobials are largely responsible for their ability to cause spoilage. Additionally, spoilage organisms can sometimes adapt to different preservatives and storage conditions, thus a combination of preservative measures can be more successful than individual measures.

There is an increasing need to develop economical, natural and effective preservative systems to meet the public demand for convenient, natural, safe, healthy, good quality products with guaranteed shelf life. Antimicrobial materials such as those derived from plants can be used as preservatives in food to help meet this need. Such plant extracts are considered to be desirable because they are regarded as being natural. Moreover from a regulatory point of view, because of long term usage, plant extracts typically have GRAS (generally regarded as safe) status. There is also a continuing to desire to provide microbial protection utilizing lower amounts of antimicrobial materials. Thus there is a need to provide new antimicrobial materials or new more effective combinations of antimicrobial materials.

Despite their natural origins, it is desirable that antimicrobial products from plants be used in the lowest possible amounts. This is desirable not only for reasons of cost but also to meet consumer desire to minimize the amount of 'additives' in foodstuffs. Moreover, many plant materials have an associated taste. Therefore in many demanding food applications reduction of the amount of protectant from plant origin is advantageous.

Meat manufacturers are looking for ways to enable them to supply retail outlets from efficient, cost effective, central-processing centers. Increased shelf life with regard to spoilage (consumer safety) is required to make this possible as meat makes its way through longer distribution channels from producer to retailer to consumer.

Color shelf life is important to consumer acceptance. Consumers judge the freshness of meat by the presence of bright red oxymyoglobin pigment. Oxymyoglobin in fresh meat decreases with time during storage as it changes to the stable brown pigment, metmyoglobin. Although oxymyoglobin pigment fades during dark storage, for example in a meat locker, pigment loss is most pronounced in lighted, refrigerated display cases in retail establishments. Further, pigment loss is primarily cosmetic in nature, it has serious economic consequences. Consumers in search of the freshest looking cuts avoid purchasing meat containing even small amounts of brown metmyoglobin.

Shelf life associated with microbial spoilage is a serious issue. The potential liability associated with food borne illness outbreaks from the sale of microbe-contaminated meat is enormous. The meat industry and associated retail outlets are seeking ways to insure consumers' safety by preventing microbial contamination all along the manufacturing process. Process improvements such as carcass washing and carefully controlled low temperature processing are now routine in the industry. One method for increasing shelf life associated with microbial spoilage is to package the food, e.g. meat, using modified atmosphere package (MAP).

There is a need in the industry for antimicrobial methods and processes which are perceived by consumers as being more natural. The antimicrobial activity of the composition comprising Lamiaceae extract and hesperidin has been the main subject of study. Most prior art indicate that the antimicrobial activity of the herbs is centered in the volatile essential oil components.

P. M. Davidson and A. S. Naidu (in Natural Food Antimicrobial Systems, A. S. Naidu, ed., 2000, CRC Press, Boca Raton, pages 265-294) review the antimicrobial properties of phyto-phenolic compounds from essential oils of spices, herbs, edible grains and seeds. The authors teach that the antimicrobial effects of spices and herbs are primarily due to the presence of phenolic compounds in the essential oil fractions and that some monoterpenes seem to show some activity, as well. Carvacrol, p-cymene and thymol are identified as the major volatile components of oregano, thyme and savory that likely account for the observed activity. The active antimicrobial agents of rosemary have been suggested to be borneol, camphor, 1,8-cineole, alpha pinene, camphene, verbenone and bornyl acetate. The active constituent of sage has been suggested to be thujone. Minimum lethal concentrations of essential oils of thyme oil have been shown to range from 225-900 ppm in cultures. These concentrations of essential oils in foods would cause serious flavor problems. Since culture experiments underestimate the concentration necessary for effectiveness in foods, the flavor problems in foods are likely to be more serious than even the culture numbers suggest. In another portion of this reference, minimum inhibitory concentrations of essential oils were stated as 1-2% for rosemary, 0.12-2% for thyme, 0.12-2% for spearmint, 0.5-2% for sage, 0.5-2% for peppermint and 0.12-2% for oregano. In the summary, the authors state that concentrations of antimicrobial compounds in herbs and spices are too low to be used effectively without adverse effects on the sensory characteristics of a food.

Y. Kimura et al. in U.S. Pat. No. 4,380,506, teach a process for producing a preservative having antioxidant and antimicrobial activity. The process involves partitioning an extract of herb spices between polar and non-polar solvents. Some of the partitioned extracts showed antimicrobial activity against Gram positive *Bacillus subtilis* microorganisms in culture media. The only taste criterion tested by Kimura et al. was the bitterness. Kimura et al. remained silent as to essential oil taste perception. Kimura et al. did not deodorize the extract which means that the extract contained essential oils and impacted the taste of the meat. This impact on taste teaches away from using rosemary extracts obtained by the process taught by Kimura et al.

D. Ninkov (WO 01/15680) teaches that pharmaceutical compositions can be prepared by combining extracts of essential oils from plants of the Lamiaceae family with an organic acid. Ninkov teaches that the antimicrobial activity of the pharmaceutical composition is due to the presence of organic phenols such as isopropyl o-cresol in the oil extract from the plant.

K. Shetty and R. G. Labbe, (Asia Pacific J. Clin. Nutr. (1998), 7(3/4), pages 270-276., describe work to clone Lamiacae plants to produce enhanced levels of essential oil components such as carvacrol and thymol. These essential oil components have some antimicrobial properties but their commercial use is prevented by the strong flavors imparted to foods by these volatile compounds.

J. Campo, M. Amiot and C. Nguyen-the (2000, Journal of Food Protection 63, pages 1359-1368) teach that rosemary extract has antimicrobial properties in culture studies. Minimum inhibitory concentrations varied with the species of bacteria being tested, but ranged from 0.06-1%. These researchers suggest that rosemary extract may show promise in foods with low fat and low protein content, against Gram positive organisms. No food systems were actually studied in this reference. This reference did not study specifically *Listeria*.

E. Down, et al., "Comparison of Vitamin E, Natural Antioxidants and Antioxidant Combinations on the Lean Color and Retail Case-Life of Ground Beef Patties" published in October, 1999, describes the effect of rosemary extract in combination with other natural antioxidants and vitamin E diet supplementation on the color life of non-MAP ground beef. This reference does not teach how to extend the microbial shelf life of the meat. The authors failed to demonstrate a red color improvement of the meat by using rosemary as the red color preservation in meat with a natural antioxidant containing rosemary could not statistically differ from the control. The red color of the control alters within commercially desirable period. The loss of as much of the red color in the control as in meat with the rosemary from this reference teaches away from using rosemary extract as stability agent capable of preserving the red color of the meat.

Ahn et al. "Effects of plant extracts on microbial growth, color change, and lipid oxidation in cooked beef", Food Microbiol., Vol. 24, Issue 1, (2007): 7-14 show that rosemary extract, or rosemary oleoresin, for which the contents in phenolic diterpenes are not known, has an antilisterial effect. In this reference, grape seed extract and pine bark extract had a greater antilisterial effect than rosemary which teaches away from using rosemary extract as the lead antilisterial natural product in meat. Further, Ahn et al. 2007 have shown that the addition of rosemary extract to meat significantly deteriorated the red color of the meat, as compared to the control that lost less of the red color or as compared to grape extract that significantly improved the preservation of the red color of the meat. Therefore, Ahn et al. 2007 teach one to not use rosemary extract as stability agent capable of preserving the red color of the meat.

United States Patent Application Publication No. 2004/131709 studies show that rosemary extract alone, Herbalox® Seasoning, in which the majority of the volatile oil components has been removed shows very little, if any, antimicrobial effect. This reference does not teach how to extend the Gram positive, more precisely antilisterial shelf life of meat.

In addition, plant derived antimicrobials from *citrus* reported in the prior art are acids not flavonoids. For example, prior patents directed to compounds from *citrus* essentially relate to acids. KR20040001441 describes orange juice as a suppressor of germ growth. However, only less than approximately $\frac{1}{50}^{th}$ of the juice reported in KR20040001441 could be used in meat without perceiving meat as sour. As meat takes up only up to 7.2% of the solution rich in citric acid, final levels in hesperidin taken up in meat would then correspond to less than 0.48%*$\frac{1}{50}$*7.2%=~0.0007%. This reference does not teach whether hesperidin could have an antilisterial effect in meat.

Lorente, José et al. "Chemical guide parameters for Spanish lemon (*Citrus limon* (L.) Burm.) juices." Food chemistry 162 (2014): 186-191 discloses that *citrus* juice has titratable acidity of 52.4 g/L, with citric acid being the main component. According to Lorente et al. (2014) in such juice, hesperidin levels as compared to titratable acidity are lower by more than two orders of magnitude (257 to 484.8 mg/L), which corresponds to 0.26 to 0.48% hesperidin w/v. Adding such an acidic composition to meat would impact the meat taste already at low levels.

Aktaş, Nesimi, and Mükerrem Kaya. "The influence of marinating with weak organic acids and salts on the intramuscular connective tissue and sensory properties of beef." European Food Research and Technology 213.2 (2001): 88-94 show that adding a solution of from 1% weak acid (including citric acid) to meat confers to the meat the sour taste. Also they show that when marinated in proportions 1:1 w/v (meat/marinade) the meat gains in weight at most 7.2% following marinating in marinades containing citric acid.

In WO 2012/112337, it is reported that flavonoids, including hesperidin, may provide some active antimicrobial activity without informing on the nature of microbes, whether they are bacteria, whether they are Gram positive bacteria nor whether they are *Listeria*. WO 2012/112337 teaches that active antimicrobial compounds are acids.

Moulehi, Ikram, et al. "Variety and ripening impact on phenolic composition and antioxidant activity of mandarin (*Citrus reticulate Blanco*) and bitter orange (*Citrus aurantium* L.) seeds extracts." Industrial Crops and Products 39 (2012): 74-80 report that *citrus* seed extracts contain total flavonoids of 1.31 to 2.52 mg equivalent catechins/g DW. As hesperidin represents <16% of total flavonoids of *citrus* seed extract, this means that hesperidin is present at ~0.032% in DW *citrus* seed extract.

Mandalari, G., et al. "Antimicrobial activity of flavonoids extracted from bergamot (*Citris bergamia* Risso) peel, a byproduct of the essential oil industry." Journal of Applied Microbiology 103.6 (2007): 2056-2064 disclose that in vitro, *citrus* extracts rich in flavonoids inhibit the growth of Gram negative bacteria only and have no effect on the growth of Gram positive bacteria, and have no effect on the growth of *Listeria*. Mandalari et al. (2007) show that neohesperidin in pure form has no effect on *Listerial* growth in vitro.

Fernandez-Lopez, J., et al. "Antioxidant and antibacterial activities of natural extracts: application in beef meatballs." Meat science 69.3 (2005): 371-380 show that meat supplemented with *citrus* extracts containing flavonoids, the main of which is hesperidin, has no effect on the growth of *Listeria monocytogenes*. For example, Fernandez-Lopez et al. (2005) show that such extracts exert antimicrobial effects on other bacterial strains, including *Listeria innocua*, but not on *Listeria monocytogenes*.

Teachings of Mandalari et al. and Fernandez-Lopez et al. teach away from using hesperidin as antilisterial compound and do not render obvious to use any or combination of flavonoids from a *citrus* extract against *Listeria monocytogenes* in meat. For example, Mandalari et al. (2007) teach away from using hesperidin as antilisterial compound and do not render obvious that a purified flavonoid could have an antilisterial effect.

*Punica* extracts rich in ellagic acid have no antimicrobial effects in raw MAP meat. For example, Hayes et al. (Hayes, J. E., Stepanyan, V., Allen, P., O'Grady, M. N., & Kerry, J. p. 2010). "Effect of lutein, sesamol, ellagic acid and olive leaf extract on the quality and shelf-life stability of packaged raw minced beef patties", Meat science, 84(4), 613-620.) (hereinafter "Hayes et al") teach that ellagic acid (one of active compounds from the *Punica* extract) has no antimicrobial effect on raw beef MAP meat stored in cold and when applied at 300 ppm. Hayes et al. teach that ellagic acid did not improve the preservation of the red color of raw beef MAP meat stored in cold and when applied at 300 ppm or at 600 ppm. Hayes et al. teach away from using lower concentrations than 300 ppm in ellagic acid for antimicrobial effect. Hayes et al. teach away from using ellagic acid for improving the red color of meat.

The general problem of enhancing the shelf life of fresh meat without impacting the taste, remains in preventing the growth of spoilage organisms and pathogens and in preserving the red color of the meat throughout the commercially desirable storage period.

SUMMARY OF THE INVENTION

According to one aspect in accordance with the present invention, compositions include a Lamiaceae (rosemary) extract comprising phenolic diterpenes wherein the extract is essentially free of the native essential oil; and *Punica* extract. In one advantageous composition, the *Punica* extract is selected from the group consisting of consisting of punicalagins and ellagic acid. Advantageously, the hesperidin extract is pure hesperidin, i.e. having a concentration of at least 80%.

Other aspects of the present method and composition are for use with a food, which includes but is not limited to meat, poultry and fish (fresh/unprocessed and processed), and comprising the components of a composition of this disclosure, a packaged food product and a method of packaging food.

The present invention, in one form thereof, relates to a composition comprising *Punica* extract and a Lamiaceae extract wherein a majority of the volatile components have been removed from the Lamiaceae extract.

The present invention, in another form thereof relates to a food which includes but is not limited to unprocessed/fresh meat, poultry and fish as well as processed meat, poultry and fish, containing a composition comprising *Punica* extract and a Lamiacea extract wherein a majority of the volatile oil components have been removed from the Lamiaceae extract.

The present invention in another form thereof relates to a method for processing, including packaging, a food. The method includes applying to or incorporating into a food which includes but is not limited to unprocessed/fresh meat, poultry and fish as well as processed meat, poultry and fish, a composition comprising *Punica* extract and a Lamiaceae extract wherein a majority of the volatile oil components have been removed from the Lamiaceae extract. Optionally, the method can further include packaging the food in an atmosphere that contains 20% or more oxygen. In alternative further embodiments, the amount of oxygen may be as much as 70% oxygen. In yet an alternative embodiment, a packaged food product comprises a food which includes but is not limited to unprocessed/fresh meat, poultry and fish as well as processed meat, poultry and fish, packaged in a standard atmospheric environment.

The present invention in another form thereof relates to a method for packaging food. The method includes applying to, or incorporating into a food, including but not limited to meat, fish or poultry (fresh/unprocessed and processed), a composition comprising *Punica* extract and a Lamiaceae extract wherein a majority of the volatile oil components have been removed from the Lamiaceae extract and the food is packaged in an environment which includes 20% or more oxygen.

In one form, the present invention is directed to the presence of *Punica* extract having a concentration of at least 95% and added 56-5380 ppm in combination with rosemary extract to meat to inhibit the growth of *Listerial monocytogenes*.

Rosemary extract in accordance with the present invention improves the preservation of the red color of meat and extends the microbial shelf life without impacting the meat flavor. The present inventors' studies in actual meat systems use a deodorized rosemary extract: an extract from which the majority of the volatile essential oil components has been removed and that does not impact the meat taste. When combined with hesperidin or with *Punica* extract, unexpectedly, synergistic antilisterial and synergistic color preservation effects are observed, without any impact on the food taste.

The present method and composition can provide ways for food manufacturers to provide retailers with products from cost-efficient, cost-effective central processing centers. The present method and composition can extend the shelf-life of fresh meat, fish and poultry, and provide fresh meat, fish and poultry that has extended microbial and color shelf-life in an atmosphere containing 70% or more oxygen and 30% or more $CO_2$. The method, in accordance with this disclosure that uses combinations of extracts can be used to improve the preservation of the meat color, block *Listerial* growth in fresh meats, fish and poultry, and allow for the use of lower, but more effective, inhibitory concentrations of plant extracts, without negative flavor impacts.

The present method is particularly suited for use with modified atmosphere packaged (MAP) meats. MAP meats are packaged in gas impermeable materials that maintain an atmosphere above the product. Mixtures of oxygen and carbon dioxide are often used in MAP meats. Mixtures of these gases work very well with the present method.

In sharp contrast to the present method and composition, the prior art teaches that *citrus* extracts containing hesperidin has no effect on *Listerial* growth in vitro nor in meat. Pure flavonoids such as hesperitin or neohesperidin do not have any effect on *Listerial* growth in vitro, nor in meat. Mandalari et al. (2007) disclose that in vitro, *citrus* extracts rich in flavonoids inhibit the growth of Gram negative bacteria only and have no effect on the growth of Gram positive bacteria, and have no effect on the growth of *Listeria*. Mandalari et al. (2007) show that neohesperidin in pure form has no effect on *Listerial* growth in vitro.

Fernandez-Lopez et al. (2005) show that meat supplemented with *citrus* extracts containing flavonoids, the main of which is hesperidin, has no effect on the growth of

*Listeria monocytogenes*. Fernandez-Lopez et al. (2005) show that such extracts exert antimicrobial effects on other bacterial strains, including *Listeria innocua*, but not on *Listeria monocytogenes*.

Teachings of Mandalari et al. and Fernandez-Lopez et al. teach away from hesperidin as antilisterial compound and do not render obvious to use any or combination of flavonoids from a *citrus* extract against *Listeria monocytogenes* in meat. Further, the teachings of Mandalari et al. teach away from hesperidin as antilisterial compound and do not render obvious that a purified flavonoid could have an antilisterial effect.

The present discloses shows that when hesperidin is concentrated at least 80% up to 99%, preference at 95%, it inhibits the growth of *Listeria monocytogenes* in meat. The prior art teaches or at the least, suggests that hesperidin does not have an effect on *Listerial* growth in meat. The present inventors found surprisingly, that hesperidin can be used in meat (e.g. minced meat) to extend its microbial, color and taste shelf life. When hesperidin alone is used, hesperidin is required to be used in higher concentrations to ensure adequate antilisterial effects. Surprisingly and unexpectedly, the addition of plant extracts comprising phenolic diterpenes to hesperidin, synergistically improves antilisterial effects and allows the use of lower doses of each extract.

Also, surprisingly, hesperidin and Lamiaceae extracts have been found to preserve color in MAP ground beef in a synergistic manner. In samples of ground beef stored 6 days in cold conditions, hesperidin plus rosemary extract exceeds the color preserving additive effect of hesperidin or rosemary alone.

The prior art is replete with statements that hesperidin containing extracts have no inhibitory effect on *Listeria monocytogenes* organisms. Surprisingly, the present inventors found evidence that hesperidin in the presence of high oxygen concentrations inhibit *Listeria monocytogenes*, Gram positive organism. The combination of hesperidin and high oxygen atmosphere inhibits *Listeria monocytogenes*, Gram positive organism isolated as a major spoilage organism in ground beef. Even more surprisingly, combinations of rosemary and hesperidin show synergistic inhibition of these *Listeria monocytogenes*, Gram positive organisms, under high oxygen atmospheres.

The combinations of Lamiaceae extract containing phenolic diterpenes and hesperidin, preserve the color of fresh meat, fish and poultry in the presence of oxygen in a synergistic manner.

Hesperidin alone at certain concentrations does not preserve the color life of fresh red meat and results in an unacceptable organoleptic feature. The combination of rosemary extract and hesperidin acts synergistically to extend the color life of ground beef in cold storage conditions. The combination is not just additive, but is synergistic, because it exceeds the additive effect of hesperidin alone and rosemary alone.

The addition of Lamiaceae extract comprising phenolic diterpenes to hesperidin, yields in flavor acceptable composition which is effective in preserving color and in inhibiting the growth of microorganisms in fresh meat, fish and poultry.

In accordance with the present disclosure, hesperidin alone suppresses *Listerial* growth in food, including meat. Further, in accordance with the present disclosure, combinations of Lamiaceae extract, preferably, rosemary extract, and hesperidin, are more effective in suppressing Gram positive, preferably *Listeria monocytogenes*, bacterial growth than either Lamiaceae extract or hesperidin, alone.

The combination of Lamiaceae extract comprising phenolic diterpenes and hesperidin in the presence of oxygen, does not impact the flavor of ground beef in a package after a commercially desirable storage period. Neither Lamiaceae extract containing phenolic diterpenes nor hesperidin alone, or oxygen alone, or a combination of two of these factors alone preserves the color as well as the combination of the three at the end of a commercially desirable storage period, without impacting the flavor.

Surprisingly, the addition of plant extracts comprising phenolic diterpenes, to hesperidin, synergistically improves antilisterial effects and allows the use of lower doses of each extract.

Also, surprisingly, hesperidin and Lamiaceae extracts have been found to preserve color in MAP ground beef in a synergistic manner. In samples of ground beef stored five (5) days in cold conditions, hesperidin plus rosemary extract exceeds the color preserving additive effect of hesperidin or rosemary alone.

The inventors found, surprisingly, that *Punica* extract containing punicalagins and ellagic acid can be used in minced meat to extend its microbial, color and taste shelf life. When *Punica* extract containing punicalagins and ellagic acid are used alone (i.e. without rosemary extract), higher concentrations of *Punica* extract are required to insure adequate antilisterial effects. Surprisingly, the addition of rosemary extracts, or extracts of other Lamiaceae synergistically improves antilisterial effects and allows the use of lower amounts of the *Punica* extract (e.g. punicalagins and ellagic acid extracts).

Also, surprisingly, *Punica* extract containing punicalagins and ellagic acid and Lamiaceae extracts have been found to preserve color in MAP ground beef in a synergistic manner. In samples of ground beef stored five (5) days in cold conditions, *Punica* extract containing punicalagins and ellagic acid plus rosemary extract exceeds the color preserving additive effect of *Punica* or rosemary alone. This synergistical effect was observed at different concentrations of each extract.

Surprisingly, the inventors found evidence that *Punica* extract containing punicalagins and ellagic acid in the presence of high oxygen concentrations inhibits *Listeria monocytogenes*, Gram positive organism. The combination of *Punica* extract containing punicalagins and ellagic acid and high oxygen atmosphere inhibits *Listeria monocytogenes*, Gram positive organism isolated as a major spoilage organism in ground beef. Even more surprisingly, the combination of rosemary and *Punica* extract containing punicalagins and ellagic acid show synergistic inhibition of these *Listeria monocytogenes*, Gram positive organisms, under high oxygen atmospheres.

The combinations of Lamiaceae extract containing phenolic diterpenes and *Punica* extract containing punicalagins and ellagic acid, extend the color shelf life of fresh meat, fish and poultry in the presence of oxygen in a synergistic manner. Critical to this invention is the combination of rosemary extract or other effective Lamiaceae extract and *Punica* extract containing punicalagins and ellagic acid, and the presence of oxygen.

*Punica* extract containing punicalagins and ellagic acid alone at certain concentrations decreases the color life of fresh red meat and results in an unacceptable organoleptic feature. The combination of rosemary extract and *Punica* extract containing punicalagins and ellagic acid acts synergistically to extend the color life of ground beef in cold storage conditions. The combination is not just additive, but is synergistic, because it exceeds the additive effect of *Punica* extract containing punicalagins and ellagic acid alone and rosemary alone.

The addition of Lamiaceae extract containing phenolic diterpenes to *Punica* extract containing punicalagins and ellagic acid, yields in flavor acceptable composition which is effective in preserving color and in inhibiting the growth of microorganisms in fresh meat, fish and poultry.

The combinations of Lamiaceae extract, preferably, rosemary extract, and *Punica* extract containing punicalagins and ellagic acid, are more effective in suppressing Gram positive, preferably *Listeria monocytogenes*, bacterial growth than either Lamiaceae extract or *Punica* extract containing punicalagins and ellagic acid, alone.

The combination of Lamiaceae extract containing phenolic diterpenes and *Punica* extract containing punicalagins and ellagic acid in the presence of oxygen, does not impact the flavor of ground beef in a package after a commercially desirable storage period. Neither Lamiaceae extract containing phenolic diterpenes nor *Punica* extract containing punicalagins and ellagic acid alone, or oxygen alone, or a combination of two of these factors alone preserves the color as well and in synergistical manner as the combination, at least up to $6^{th}$ day of storage, without impacting the flavor.

Surprisingly, the addition of rosemary extracts, or extracts of other Lamiaceae synergistically improves antilisterial effects and allows the use of lower doses of each extract.

Also, surprisingly, *Punica* extract containing punicalagins and ellagic acid and Lamiaceae extracts have been found to preserve color in MAP ground beef in a synergistic manner. In samples of ground beef stored five (5) days in cold conditions, *Punica* extract containing punicalagins and ellagic acid plus rosemary extract exceeds the color preserving additive effect of hesperidin or rosemary alone.

Surprisingly, the inventors found evidence that *Punica* extract containing punicalagins and ellagic acid in the presence of high oxygen concentrations inhibit *Listeria monocytogenes*, Gram positive organism. The combination of *Punica* extract containing punicalagins and ellagic acid and high oxygen atmosphere inhibits *Listeria monocytogenes*, Gram positive organism isolated as a major spoilage organism in ground beef. Even more surprisingly, the combination of rosemary and *Punica* extract containing punicalagins and ellagic acid show synergistic inhibition of these *Listeria monocytogenes*, Gram positive organisms, under high oxygen atmospheres.

The combinations of Lamiaceae extract containing phenolic diterpenes and *Punica* extract containing punicalagins and ellagic acid, preserve the color of fresh meat, fish and poultry in the presence of oxygen in a synergistic manner. Accordingly, advantageous to some of the present methods and compositions of this disclosure is a combination of rosemary extract or other effective Lamiaceae extract and *Punica* extract containing punicalagins and ellagic acid, and the presence of oxygen.

*Punica* extract containing punicalagins and ellagic acid alone at certain concentrations decreases the color life of fresh red meat and results in an unacceptable organoleptic feature. The combination of rosemary extract and *Punica* extract containing punicalagins and ellagic acid acts synergistically to extend the color life of ground beef in cold storage conditions. The combination is not just additive, but is synergistic, because it exceeds the additive effect of *Punica* extract containing punicalagins and ellagic acid alone and rosemary alone.

The addition of Lamiaceae extract containing phenolic diterpenes to *Punica* extract containing punicalagins and ellagic acid, yields in flavor acceptable composition which is effective in preserving color and in inhibiting the growth of microorganisms in fresh meat, fish and poultry.

The combinations of Lamiaceae extract, preferably, rosemary extract, and *Punica* extract containing punicalagins and ellagic acid, are more effective in synergistical manner in suppressing Gram positive, preferably *Listeria monocytogenes*, bacterial growth than either Lamiaceae extract or *Punica* extract containing punicalagins and ellagic acid, alone. Neither Lamiaceae extract containing phenolic diterpenes nor *Punica* extract containing punicalagins and ellagic acid alone, or oxygen alone, or a combination of two of these factors alone preserves the meat against *Listeria monocytogenes* as well as the combination of the three, within commercially desirable storage period, without impacting the flavor.

The combination of Lamiaceae extract containing phenolic diterpenes and *Punica* extract containing punicalagins and ellagic acid in the presence of oxygen, does not impact the flavor of ground beef in a package after a commercially desirable storage period. Neither Lamiaceae extract containing phenolic diterpenes nor *Punica* extract containing punicalagins and ellagic acid alone, or oxygen alone, or a combination of two of these factors alone preserves the color as well as the combination of the three after five (5) days of cold storage period, without impacting the flavor.

To keep the number of additives within reasonable bounds with respect to meat, fish or poultry, it is advantageous to use botanical extracts that provide the property of inhibiting the growth of *Listeria monocytogenes*, and, more particularly, it is advantageous to combine botanical extracts that provide synergistic antilisterial effects and that preserve the red color of the meat without impacting the meat taste. Advantageously, formulations of different botanical extracts, in accordance with this disclosure, function synergistically to increase the total antilisterial activity and to preserve the red color of the meat without impacting the meat taste, of the combined extracts, that are superior to the sum of their individual contributions.

The methods and compositions in accordance with the present disclosure, exhibit a synergistic effect, as introduced above and will be discussed in more details to follow. It is noted that in contrast to the synergistic effect of the methods and compositions in accordance with the present disclosure, when two compounds elicit the same overt response, regardless of the mechanism of action and the combined effect is the algebraic sum of their individual effects, the compounds are said to exhibit summation (Levine et al., 1996). However, in synergism, the joint effect of two compounds is greater than the algebraic sum of their individual effects.

The technique in Levine et al. (1996) has been used to evaluate biological effects of compound combinations. Shown in FIG. 1 (identified as "Prior Art" and taken from Basic Principles of Pharmacology, Tulane University), top graph, compound combination effects illustrate that when two compounds with similar mechanisms are given together, they typically produce additive effects. This is also referred to as summation. However, if the effect of two compounds exceeds the sum of their individual effects, this is an unexpected effect referred to synergism.

By analogy, a synergistic response concerning half doses, as illustrated in the bottom graph of FIG. 1, occurs if the combination of half the dose of compound A and B produces a response greater than A or B alone.

Those skilled in the art of antimicrobial formulations for food matrices such as meat, are aware that antimicrobial synergy in meat is not predictable. Not a single synergy could be disclosed for different combinations between three natural botanical extracts. Gutierrez, J., Barry-Ryan, C., & Bourke, P. (2008). "The antimicrobial efficacy of plant essential oil combinations and interactions with food ingredients." *International journal of food microbiology*, 124(1), 91-97). Synergistic effects of combinations have rarely been disclosed for combinations between synthetic and natural extracts (see e.g. WO 2013/169231).

One advantage of some compositions and methods, in accordance with this disclosure, is achieved by a process which removes volatile compounds by deodorization. The deodorization process removes volatile compounds including borneol, camphor, 1,8-cineole, alpha pinene, camphene, verbenone and bornyl acetate.

An additional advantage, in accordance with some aspects of the present methods, systems and compositions of this disclosure, is achieved through a combination of hesperidin or *punica* extract with lamiaceae extract. Further, unlike the process described in U.S. Pat. No. 4,380,506, methods, in accordance with this disclosure, do not require the partitioning process and the methods avoid the use of additional processing expense.

An additional advantage in accordance with one aspect of the present method and system, is a composition which reduces the concentration of volatile compounds to a low level so as to not impact the taste of a food product to which a composition is applied such as meat, thereby not affecting the taste of the meat.

One additional advantage of some aspects of the present invention is the presence of *punica* extract with more than 60 full lower concentration in ellagic acid (than previously reported by Hayes et al) resulting in anti-*listerial* effects when combined with rosemary extract.

DETAILED DESCRIPTION OF THE INVENTION

Figure 1:
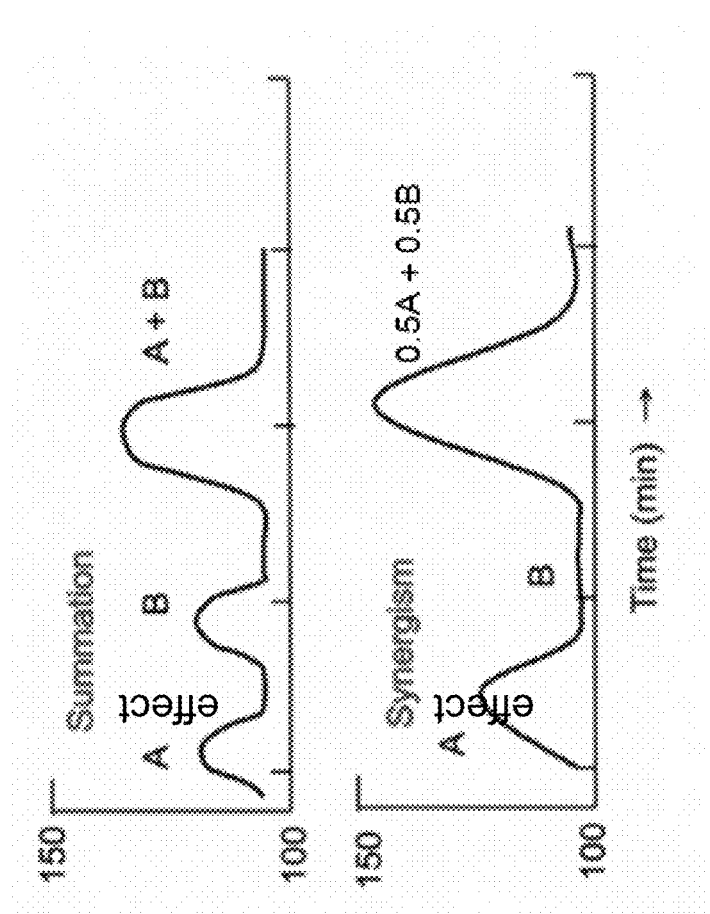
FIG. 1 is adapted from "Basic Principles of Pharmacology", (Tulane University), in which the top portion is "Summation: Compounds A and B Produce Equal Effects, And Their Affects Are Additive When Combined" and the bottom portion is "Synergism: The Combination of Half the Dose of Compound A and Compound B Produces a Response Greater Than A or B Alone."

Compositions in accordance with this disclosure include Lamiaceae extract and hesperidin and methods for using compositions for extending the shelf life of fresh meat, fish and poultry without impacting the taste.

The present invention in another form, includes compositions comprising Lamiaceae extract and *Punica* extract and methods for using these compositions for extending the shelf life of fresh meat, fish and poultry without impacting the taste.

The present methods and compositions are based on a discovery that rosemary extracts rich in phenolic diterpenes, alone, or in combination with hesperidin or with *Punica* extracts rich in ellagic acid and in punicalagins, preserve the red color of the meat for commercially significant period. The present inventors discovered that treating meat with pure hesperidin, that is a flavonoid, extracted from *citrus* peels and then purified, prevents the growth of *Listeria monocytogenes* in meat. Lamiaceae extracts comprising phenolic diterpenes in combination with hesperidin or with *Punica* extract comprising ellagic acid and punicalagins, synergistically provided novel solutions for suppressing the growth of microorganisms for a commercially desirable period and for preserving the red color of the meat without impacting the meat taste. Compositions of this invention have been found to inhibit the growth of Gram positive microorganisms. Compositions of this invention, have been found to inhibit the growth of *Listeria*. Compositions of this invention, have been found to inhibit the growth of *Listeria monocytogenes*.

Combinations comprising: plant extracts standardized in phenolic diterpenes carnosic acid and carnosol, and hesperidin, or plant extracts standardized in phenolic diterpenes carnosic acid and carnosol, and plant extracts standardized in ellagic acid and punicalagins, that would have been used to synergistically prevent *Listeria monocytogenes* growth in meat without impacting the meat taste and that synergistically improve the preservation of the meat color, could not be retrieved from the prior art.

None of the prior art on the antimicrobial use of the combination of rosemary or other Lamiaceae extracts comprising phenolic diterpenes with hesperidin or with *Punica* extracts comprising punicalagins and ellagic acid, either anticipates or renders obvious the present methods and compositions. The prior art focuses on the use of herb essential oils or on the use of organic acids, such as *citric* acid. The rosemary extracts used in the present disclosure are processed in a manner that makes them essentially free of the native essential oil and rich in phenolic diterpenes. The prior art neither anticipates nor renders obvious the synergistic combination of Lamiaceae extracts rich in phenolic diterpenes and *Punica* extracts rich in punicalagins and ellagic acid.

The prior art neither anticipates nor renders obvious the synergistic combination of Lamiaceae extracts rich in phenolic diterpenes and hesperidin. The prior art neither anticipates nor renders obvious the surprisingly beneficial antimicrobial effect of the combination of Lamiaceae extracts comprising phenolic diterpenes with *Punica* extracts comprising punicalagins and ellagic acid, or with hesperidin, on Gram positive organisms: *Listeria monocytogenes*. The prior art neither anticipates nor renders obvious the surprisingly beneficial color preservation effect of the combination of Lamiaceae extracts comprising phenolic diterpenes with *Punica* extract comprising punicalagins and ellagic acid, or with hesperidin.

The prior art neither anticipates nor renders obvious the absence of the impact on food taste of the combination of Lamiaceae extracts comprising phenolic diterpenes with *Punica* extract comprising punicalagins and ellagic acid, or with hesperidin.

Other flavonoids that have the same effect including but are not limited to: narigin, isocurametin, neohesperidin, hesperidin, poncirin, nebiletin, and tangeretin.

Definitions

The following are a list of definitions used throughout this disclosure:

"Effective amount" is the amount necessary in order to achieve a specific effect, in accordance with what one of ordinary skill in the art would be readily able to determine through routine experimentation. For example, with regard to the present disclosure, an effective amount of a composition comprising *Punica* extract and a Lamiaceae extract to be applied to fresh meat, fish and poultry, to extend the longevity of red color to the fresh meat, fish and poultry, is an amount which is determined to provide the red color longevity based on known parameters which include, but are not limited to the concentration of *Punica* and a Lamiaceae extract, the volume and/or surface area of the fresh meat, fish and poultry, and the atmospheric environment conditions of the fresh meat, fish and poultry. Similarly, the effective amounts of rosemary/*Punica* to extend the longevity of other foods are determined in a similar way.

"Food" and "food product" mean products that people or animals eat. The food or food product include, but are not limited to fresh meat, fish and poultry and processed meat, fish and poultry.

"Fresh meat, fish, and poultry" means meat fish and poultry, entire carcasses, cut portions thereof, and ground portions thereof. Fresh meat, fish, and poultry includes both unprocessed meat, fish and poultry as well as meat, fish, and poultry that includes additives such as polyphosphates, salt, water, flavors, broths, added proteins, sugar, starches and the like which are incorporated into the meat, fish or poultry. It is important to distinguish fresh meat, fish or poultry which may contain these ingredients, from cured meat, fish and poultry, which may contain the same ingredients, but also contain one or more of the following: erythorbates, erythorbic acid, ascorbates, ascorbic acid, nitrites, nitrates or cultures. Fresh meat, fish and poultry are to be distinguished from, and as opposed to, and does not include cured meat, fish or poultry.

"Hesperidin" means a compound extracted from nature or synthesized.

"Lamiaceae extract" means extract from a plant of the Lamiaceae family, preferably rosemary, sage, oregano, thyme, mints, and the following genera: *Salvia, Rosmarinus, Lepechinia, Oreganum, Thymus, Hyssopus* and mixtures thereof. The most preferred is rosemary.

"Meat, fish and poultry to means both a) processed meat, fish and poultry and b) unprocessed meat, fish and poultry.

"Phenolic diterpenes" means carnosic acid, carnosol, methylcarnosate, and other phenolic diterpene derivatives (rosmanol, isorosmanol, 11,12-di-O-methylisorosmanol, 12-O-methylcarnosic acid, rosmanol-9-ethyl ether, circimaritin, Methylated monooxidized product of carnosic acid, genkwanin, epirosmanol, epiisorosmanol, carnosic acid derivative, epirosmanol ethyl ether, cryptotanshinone) and mixtures thereof.

"Processed" such as "processed foodstuff" and "processed meat, fish and poultry" are products resulting from the processing of food, such as meat, fish or poultry or from the further processing of such processed products, so that the cut surface shows that the product no longer has the characteristics of fresh meat, fish or poultry. Processing means any action that substantially alters the initial product, including heating, smoking, curing, maturing, drying, marinating, extraction, extrusion or a combination of those processes. Processes include non-heat treated and heat-treated processes.

"*Punica* extract" means extract from a plant of the *Punica* genus, preferably *Punica granatum* and *Punica protopunica*, and mixtures thereof. The most preferred is *Punica granatum*.

"Unprocessed" (such as meat, fish and poultry) means not having undergone any treatment resulting in a substantial change in the original state of the foodstuffs (e.g. meat, fish and poultry). However, the foodstuffs may have been for example divided, parted, severed, boned, minced, skinned, pared, peeled, ground, cut, cleaned, trimmed, deep-frozen, frozen, chilled, milled or husked, packed or unpacked. Unprocessed foodstuff, including meat, fish and poultry include untreated raw meat, fish and poultry, as well as fresh meat, fish and poultry that has been comminuted or minced, that has had foodstuffs seasons or additives added to it or that has undergone processing insufficient to modify the internal muscle fiber of the meat, fish or poultry and thus eliminate the characteristics of fresh meat, fish or poultry.

In the development of the present method and composition, it was discovered that hesperidin has an antilisterial effect in meat when prepared within certain ranges of concentrations.

In the development of the present method and composition, it was discovered that rosemary extract comprising phenolic diterpenes combined with hesperidin or with *Punica* extract has a superior effect on suppressing the growth of *Listeria monocytogenes* in meat than when extracts are applied alone.

In the development of the present method and composition, it was discovered that certain mixtures of extracts of the rosemary combined with hesperidin or with *Punica* extract comprising punicalagins and ellagic acid, provide a synergistic antilisterial effect when prepared within certain ranges of concentration ratios.

In the development of the present method and composition, it was discovered that rosemary extract comprising phenolic diterpenes combined with hesperidin or with *Punica* extract has a superior effect on preserving the red color in meat than when extracts are applied alone.

In the development of the present method and composition, it was discovered that certain mixtures of extracts of the rosemary combined with hesperidin or with *Punica* extract comprising punicalagins and ellagic acid, provide a synergistic red color preservation effect in meat when prepared within certain ranges of concentration ratios.

Mixtures of Extracts Rich in Phenolic Diterpenes and Hesperidin or *Punica* Extract Phenolic diterpenes such as carnosic acid or carnosol occur specifically in Lamiaceae. To date, carnosic acid has been identified in only a few species, all exclusive of the Lamiaceae. To the best of the inventors' knowledge, only seven out of 70 genera of the Mentheae tribe contain carnosic acid: *Salvia* (Brieskorn and Dumling, 1969), *Rosmarinus* (Luis and Johnson, 2005), *Lepechinia* (Bruno et al., 1991), *Oreganum* (Hossain et al., 2010) and *Thymus* (Achour et al., 2012). It may be present in *Hyssopus* where one of its possible derivatives, rosmanol-9-ethyl ether (7), was identified (Djarmati et al., 1991). Carnosic acid also occurs as a minor compound in one genus of the Ocimeae tribe, *Ocimum* (Jayasinghe et al., 2003). Brieskorn, C. H., Dumling, H. J., 1969. Carnosolsaure, der wichtige antioxydativ wirksame Inhaltsstoff des Rosmarin-und Salbeiblattes. Zeitschrift fur Lebensmittel-Untersuchung and Forschung 141, 10-16; Luis, J. C., Johnson, C. B., 2005; Bruno, Maurizio, et al. "Abietane diterpenoids from *Lepechinia meyeni* and *Lepechinia hastata*." Phytochemistry 30.7 (1991): 2339-2343; Hossain, Mohammad B., et al. "Characterization of phenolic composition in Lamiaceae spices by LC-ESI-MS/MS." Journal of agricultural and food chemistry 58.19 (2010): 10576-10581; Achour, S., Khelifi, E., Attia, Y., Ferjani, E., Noureddine Hellah A., 2012. Concentration of Antioxidant Polyphenols from *Thymus capitatus* extracts by Membrane Process Technology. Journal of food science 77, C703-C709; Djarmati, Z., Jankov, R. M., Schwirtlich, E., Djulinac, B., Djordejevic, A., 1991. High antioxidant activity of extracts obtained from sage by supercritical $CO_2$ extracton. Journal of the American Oil Chemists Society 68, 731-734; Jayasinghe, C., Gotoh, N., Aoki, T., Wada, S., 2003. Phenolic composition and antioxidant activity of sweet basil (*Ocimum basilicum* L.). Journal of agricultural and food chemistry 51, 4442-4449. Seasonal variations of rosmarinic and carnosic acids in rosemary extracts. Analysis of their in vitro antiradical activity. Spanish Journal of Agricultural Research 3, 106-112.

Here these phenolic diterpenes were extracted from rosemary with the aim of extracting and concentrating essentially phenolic diterpenes: 44-85%. Thus obtained extract was then deodorized in order to get rid of essential oils and volatile compounds that impact the food taste.

Rosemary Extract

Rosemary (*Rosmarinus officinalis*) leaves can be extracted with various solvents and yield extracts that are rich in different compounds. For instance, aqueous extracts are rather abundant in rosmarinic acid whereas extractions using organic solvents rather yield in extracts rich in phenolic diterpenes such as carnosic acid and carnosol. The detailed procedure to prepare the composition of Rosemary extract was described in the U.S. Pat. No. 5,859,293 and WO 96/34534, both herein incorporated by reference.

The rosemary leaf was extracted with acetone at room temperature. After the extraction was completed, the acetone extract was filtered to separate the solution from rosemary leaf and concentrated under reduced pressure to make concentrated native extract. At this time, the concentrated extract can be dried directly in a vacuum oven under mild heat to make a powdered extract, which is a composition comprising about 15%-30% carnosic acid and 1%-3% carnosol. Alternatively, to the concentrated native extract, aqueous sodium carbonate ($NaHCO_3$) was added to dissolve carnosic acid and other organic acids, while base insoluble substances were precipitated out.

The solution was filtered to separate from solid, and the filtrate was further concentrated under reduced pressure. Once finishing concentration is achieved, phosphoric acid ($H_3PO_4$) was added and the acid insoluble substances (including carnosic acid, carnosol, and carnosic derivatives) were precipitated from the concentrated solution. Charcoal active is used during the process to decolorize the rosemary extract in solution before filtration. Through filtering, the precipitated solid was subsequently separated from liquid and rinsed with water to remove impurities.

Last, the solid was dried in a vacuum oven and then milled into powder to make a composition containing about 40-65% carnosic acid, 2-10% carnosol, and 2-10% 12-O-methylcarnosic acid. Here used extract contained >48% carnosic acid+carnosol. A last step was done to deodorize the rosemary extract. It corresponded to a subsequent extraction of the previous solid with a mix of acetone/hexane. The purpose of this step was the elimination of fatty molecules and of volatile compounds. The filtrate was concentrated under reduced pressure and was directly formulated on liquid carrier.

Within the present specification and claims, this extract standardized in phenolic diterpenes carnosic acid and carnosol, will be referred to either as rosemary, or rosemary extract or rosemary (powder) or rosemary (liquid).

Hesperidin Extraction

Dried immature fruits (*citrus aurantium* L.) were exposed to a vapor in order to remove pectins prior to the extraction with water. Subsequently, sodium hydroxide and calcium hydroxide were added in the solution to stabilize the pH value. Following the filtration step, an acidification of the filtrate was induced using HCl. Upon this step the hesperidin precipitates, the liquid solution is removed and the precipitate is dried. The final product contains 90% to 99% hesperidin, preferably more than 95% of hesperidin as measured by HPLC.

The obtained extracts contain essentially hesperidin (>80%) and are considered to be pure. Throughout this disclosure, this extract standardized in hesperidin at >95%, will be referred to as hesperidin or hesperidin (powder) or hesperidin (liquid).

*Punica* Extraction

Pomegranate skin bitter (*Punica granatum* L.) was extracted with ethanol/water. The extract was filtered, then concentrated. The extract was mixed with a carrier, in this example with maltodextrin prior to drying. Different drying technologies can be applied. This extract was standardized in following polyphenols: punicalagins (>7.5% by HPLC) and ellagic acid (1.5-2.5%) as determined by HPLC.

Throughout this disclosure, this extract standardized in punicalagins (>7.5% by HPLC) and ellagic acid (1.5-2.5%), will be referred to either as *Punica*, or *Punica* extract or *Punica* (powder) or *Punica* (liquid).

Preparation of Products and Mixtures of Rosemary Extract/Hesperidin and Rosemary Extract/*Punica* Extract Plant extracts and their combinations were dried into powders. Maltodextrin was used in order to insure the suitable drying process of combinations of extracts. Maltodextrins are commonly used excipients or carriers for drying processes.

Maltodextrins are defined as starch hydrolysis products with dextrose equivalent less than 20. Dextrose equivalent (DE value) is a measure of the reducing power of starch derived oligosaccharides expressed as percentage of D-glucose on dry matter of hydrolysate and is inverse value of average degree of polymerisation (DP) of anhydro glucose units. As products of starch hydrolysis, maltodextrins contain linear amylose and branched amylopectin degradation products, therefore they are considered as D-glucose polymers joined by a-(1,4) and a-(1,6) linkages.

Although maltodextrins are derived from a natural compound (starch), their structure is different from the initial structure of the natural molecule they derive from (starch). This difference is induced by the hydrolysis process. Thus, maltodextrin structure does not occur in nature.

Other possible excipients or carriers include maltodextrin, arabic gum, dextrose, salt, mono & diglycerides of fatty acids, MPG, Polysorbate 80, vegetable oil, mono & diglycerides of fatty acids, glucose syrup, glycerin, water and alcohol.

Compositions Were Added to the Raw Minced Beef Meat at 15% fat.

Figure 2:
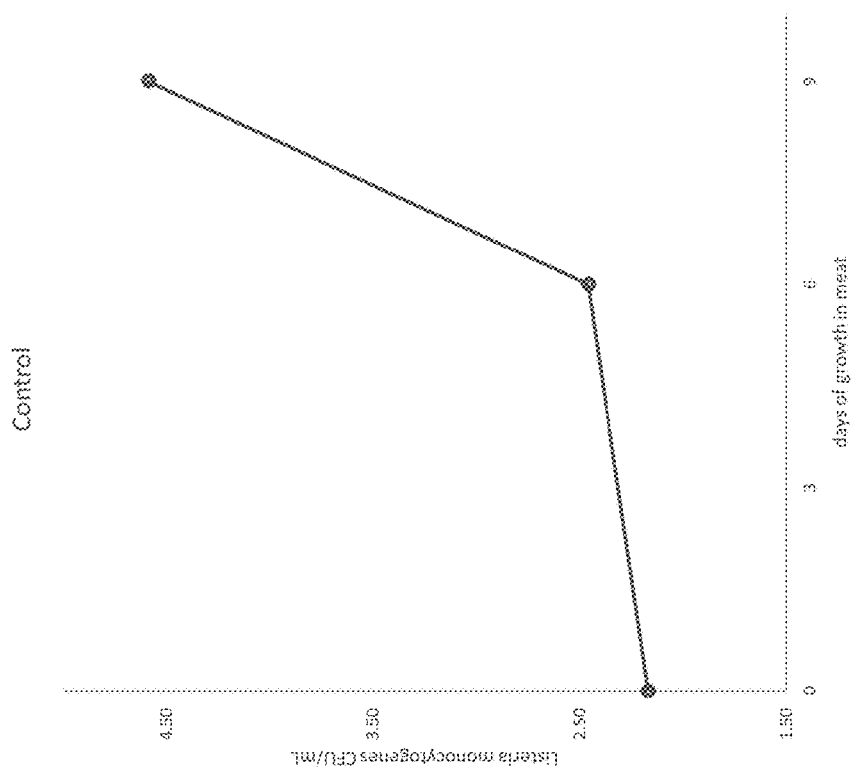
FIG. 2 is a graph showing *Listeria monocytogenes* growth in meat in accordance with the present invention.

In the course of the work leading to the present method and composition, mixtures of rosemary extract and of hesperidin or of *Punica* extract, in a number of varying concentration ratios were tested for antilisterial effectiveness using the classical microbiological methods. Bacterial enumeration in all here studied samples was performed on the Aloa medium according to the standardized method (NF EN ISO 11-290). The growth of *Listeria monocytogenes* was evaluated in meat without any antilisterial agent and without any plant extract (control). The data of *listerial* growth in a control meat are represented in FIG. 2. It will be noted that after 6 days of growth *Listeria* grew slightly, only by 0.29 log CFU/mL. After 9 days of growth, *Listeria* grew by 2.42 log CFU/mL. Experiments on meat were conducted in modified atmosphere packagings (MAP) that contained more than 20% $O_2$, more precisely 70% $O_2$ and 30% $CO_2$.

Following the meat manufacture, a batch of meat was sampled straight after the mincing process and transported in refrigerated conditions to the laboratory. In the laboratory, the meat was sampled into 2 kg samples and conditioned in vacuum at −20° C., 24 h prior to experimentation, the 2 kg meat samples were transferred at 2-4° C. and kept at this temperature for 24 h±3 h until the core temperature attained −1° C.

At this stage the 2 kg meat samples were inoculated with *Listeria monocytogenes* in a laboratory of a biosafety of level 3 so that the contamination by other microorganisms was avoided. Any further supplementation to the meat was conducted in such a laboratory. Following the homogenization of the inoculum at 4° C., the inoculated 2 kg meat samples were supplemented with plant extracts and homogenised. Plant extracts were in powder form and were added as such to the meat. To keep them as dry powders, plant extracts were supplemented with maltodextrin prior to drying process.

Plant extracts could be added as lipophilic or hydrophilic liquids, or combinations thereof, to the meat. To do so, plant lipophilic or hydrophilic extract need to be solubilized or liquid, undried extracts could be used directly without undergoing the drying step.

Immediately after the supplementation of plant extracts and homogenisation, two pieces of 100 g of thus formed minced meat were placed together in trays. Control meat pieces, without extract treatment, followed the same procedure.

Trays were then conditioned under modified atmosphere of 20% or more of oxygen, preferably 70% $O_2$ and 30% $CO_2$ at 4 or at 8° C. Packaged meat was stored in the dark for a stated amount of time.

A series of experiments involving rosemary and hesperidin extracts, rosemary and *Punica* extracts, typical antilisterial compounds (Sodium lactate or Sodium acetate) and untreated control were conducted. Mixtures or alone extracts of rosemary and of hesperidin were added at 1.18% to the meat. Mixtures or alone extracts of rosemary and of *Punica* were added at 0.48% to the meat. Typical antilisterial compounds, Sodium lactate and Sodium acetate, were added at classic concentrations 25 g/kg and 3 g/kg, respectively, in separate experiments.

Combinations of extracts were prepared and added to the meat according to the following proportions and doses prior to testing:

|  |  | Control LM | 0.5R | R | 0.5H | H | 0.5R + 0.5H | 0.5R + H | R + 0.5H | R + H |
|---|---|---|---|---|---|---|---|---|---|---|
| Composition of extracts (%) | Rosemary extract | 0.00 | 1.28 | 2.56 | 0.00 | 0.00 | 1.28 | 1.28 | 2.56 | 2.56 |
|  | Carnosic acid | 0.00 | 0.56 | 1.13 | 0.00 | 0.00 | 0.56 | 0.56 | 1.13 | 1.13 |
|  | Carnosic acid + carnosol | 0.00 | 0.62 | 1.24 | 0.00 | 0.00 | 0.62 | 0.62 | 1.24 | 1.24 |
|  | Hesperidin extract | 0.00 | 0.00 | 0.00 | 24.00 | 49.00 | 24.00 | 48.00 | 24.00 | 48.00 |
|  | Hesperidin | 0.00 | 0.00 | 0.00 | 22.80 | 46.55 | 22.80 | 45.60 | 22.80 | 45.60 |
| Composition in minced beef (ppm) | Rosemary extract | 0 | 151 | 302 | 0 | 0 | 151 | 151 | 302 | 302 |
|  | Carnosic acid | 0 | 66 | 133 | 0 | 0 | 66 | 66 | 133 | 133 |
|  | Carnosic acid + carnosol | 0 | 73 | 146 | 0 | 0 | 73 | 73 | 146 | 146 |
|  | Hesperidin extract | 0 | 0 | 0 | 2832 | 5782 | 2832 | 5664 | 2832 | 5664 |
|  | Hesperidin | 0 | 0 | 0 | 2690 | 5493 | 2690 | 5381 | 2690 | 5381 |

R: rosemary extract;
H: hesperidin;
0.5R: half concentration of rosemary extract;
0.5H: half concentration of hesperidin;
R: rosemary extract;
P: *Punica* extract;
0.5R: half concentration of rosemary extract;
0.5P: half concentration of *Punica* extract

|  |  | Control LM | 0.5R | R | 0.5P | P | 0.5R + 0.5P | 0.5R + P | R + 0.5P | R + P |
| --- | --- | --- | --- | --- | --- | --- | --- | --- | --- | --- |
| Composition of extracts (%) | Rosemary extract | 0.00 | 3.33 | 6.65 | 0.00 | 0.00 | 3.33 | 3.33 | 6.65 | 6.65 |
|  | Carnosic acid | 0.00 | 1.47 | 2.93 | 0.00 | 0.00 | 1.47 | 1.47 | 2.93 | 2.93 |
|  | Carnosic acid + carnosol | 0.00 | 1.61 | 3.22 | 0.00 | 0.00 | 1.61 | 1.61 | 3.22 | 3.22 |
|  | Pomegranate extract | 0.00 | 0.00 | 0.00 | 13.50 | 7.00 | 13.50 | 27.00 | 13.50 | 27.00 |
|  | Ellagic acid | 0.00 | 0.00 | 0.00 | 0.27 | 0.54 | 0.27 | 0.54 | 0.27 | 0.54 |
|  | Punicalagins | 0.00 | 0.00 | 0.00 | 1.22 | 2.43 | 1.22 | 2.43 | 1.22 | 2.43 |
| Composition in minced beef (ppm) | Rosemary extract | 0 | 160 | 319 | 0 | 0 | 160 | 160 | 319 | 319 |
|  | Carnosic acid | 0 | 70 | 140 | 0 | 0 | 70 | 70 | 140 | 140 |
|  | Carnosic acid + carnosol | 0 | 77 | 154 | 0 | 0 | 77 | 77 | 154 | 154 |
|  | Pomegranate extract | 0 | 0 | 0 | 648 | 1296 | 648 | 1296 | 648 | 1296 |
|  | Ellagic acid | 0 | 0 | 0 | 13 | 26 | 13 | 26 | 13 | 26 |
|  | Punicalagins | 0 | 0 | 0 | 58 | 117 | 58 | 117 | 58 | 117 |

Immediately after the supplementation and the homogenization, two pieces of 100 g minced meat in shape of hamburgers were placed in trays. The trays were then conditioned in a modified atmosphere containing 70% $O_2$ and 30% $CO_2$ and stored at 8° C. until analysis of Listerial growth and of organoleptic features, including the red color. Such analyses were conducted on the $0^{th}$, $6^{th}$ and $9^{th}$ day of storage.

The growth of Listeria monocytogenes was evaluated in meat in refrigerated conditions for each extract or compound and for their combinations. The growth of Listeria monocytogenes was measured at the beginning of the experiment, at ⅔rd of the commercial shelf life (6 days) and at the time point corresponding to the commercial duration of the shelf life (9 days). Logarithmic values of Listerial growth (log CFU/mL) were calculated for each experiment and treatment. Differences of logarithmic values of Listerial growth (log CFU/mL) between the meat treated with plant extracts and the untreated control were calculated to yield a final result. The more negative value was obtained, the higher was the antilisterial effect of the extract or of the combination of extracts. In meat science microbiology, for a given time, values are considered to be significant between two series when a difference of 0.5 Log 10 $CFU \cdot g^{-1}$ is observed (Chaillou et al., 2014); (Guide pour la validation de méthodes d'essais microbiologiques et l'évaluation de leur incertitude de mesure dans les domaines de la microbiologie alimentaire et de l'environnement), Schweizerische Eidgenossenschaft, Confédération suisse, Département fédéral de l'économie, de la formation et de la recherche DEFR, Document No. 328, April 2013, Rev. 03). In microbiology, it will be noted that a treatment has a significant antibacterial effect if its effect exceeds −0.5 log CFU/mL as compared to the untreated control.

During the listerial growth, color of meat was monitored and images were taken straight after the addition of the extract (on the day 0) and on the $6^{th}$ day of growth). Images were taken under standardized light conditions of exposure and using a system called "PackShot Creator." Indeed, this professional equipment consists of an optimized light box containing four fluorescent tubes diffusing homogeneous light, resulting in images always taken under the same conditions, with minimal reflection.

Each picture representing the "sample" at a different time scale was loaded in the open source image analysis program ImageJ. The software is commonly used in the food industry to measure different food parameters such as color or density (Reineke et al. "The Influence of Sugars on Pressure Induced Starch Gelatinization, Procedia Food Science, 1, 2011, 2040-3046; Kelkar et al. "Developing novel 3D measurement techniques and prediction method for food density determination, Procedia Food Science, 1, 2011, 483-491). In order to obtain representative values of the red color, the color unit red (R) out of the three color units red (R) green (G) and blue (B) of the RGB model was used, and the color was measured of each pixel of a line that was drawn across the sample. The inbuilt RGB profile plot plugging was used to determine the different color values of each pixel along this line, notably the values of the red color. The results are presented as variation of the different color value as a function of the pixel number along this line. The results were statistically analyzed for significant differences using ANOVA test at $p<0.05$. Thus, per sample, more than 1000 pixels were analyzed.

In order to evaluate the effect of plant extracts on the color of the meat, red color of the treated meat was compared to an untreated control. The effect was calculated by [red color in meat with extract]−[red color in control meat (without extract)]. Negative effect means that the addition of extracts does not preserve the red color of the meat. Positive effect means that the addition of extracts improves the red color of the meat as compared to the control.

Mixtures of Rosemary and Hesperdin

Growth of Listeria monocytogenes in Raw Meat

Figure 7:
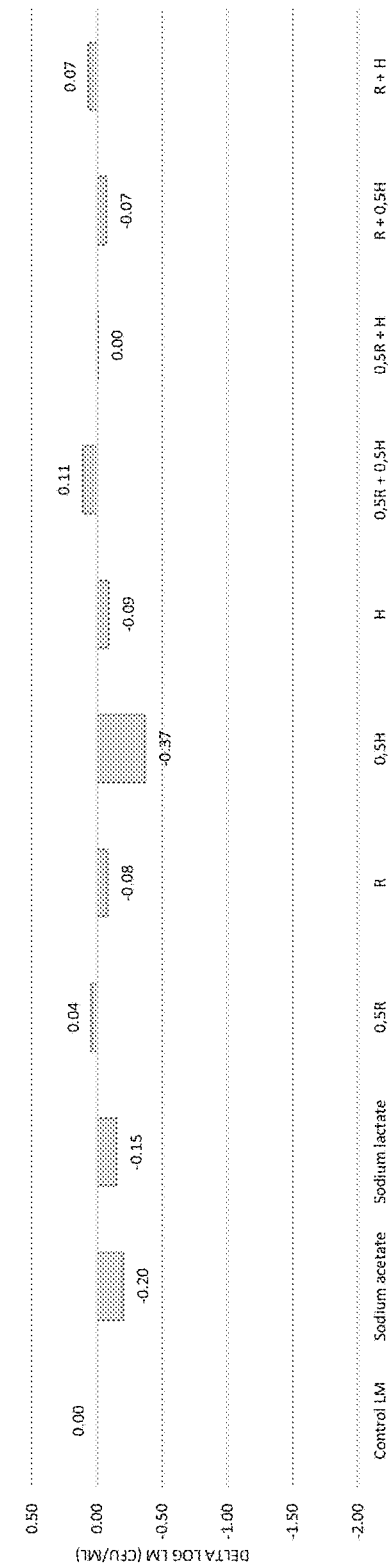
FIG. 7 is a chart showing inhibition of *Listeria monocytogenes* growth by plant extracts in minced beef.
Figure 8:
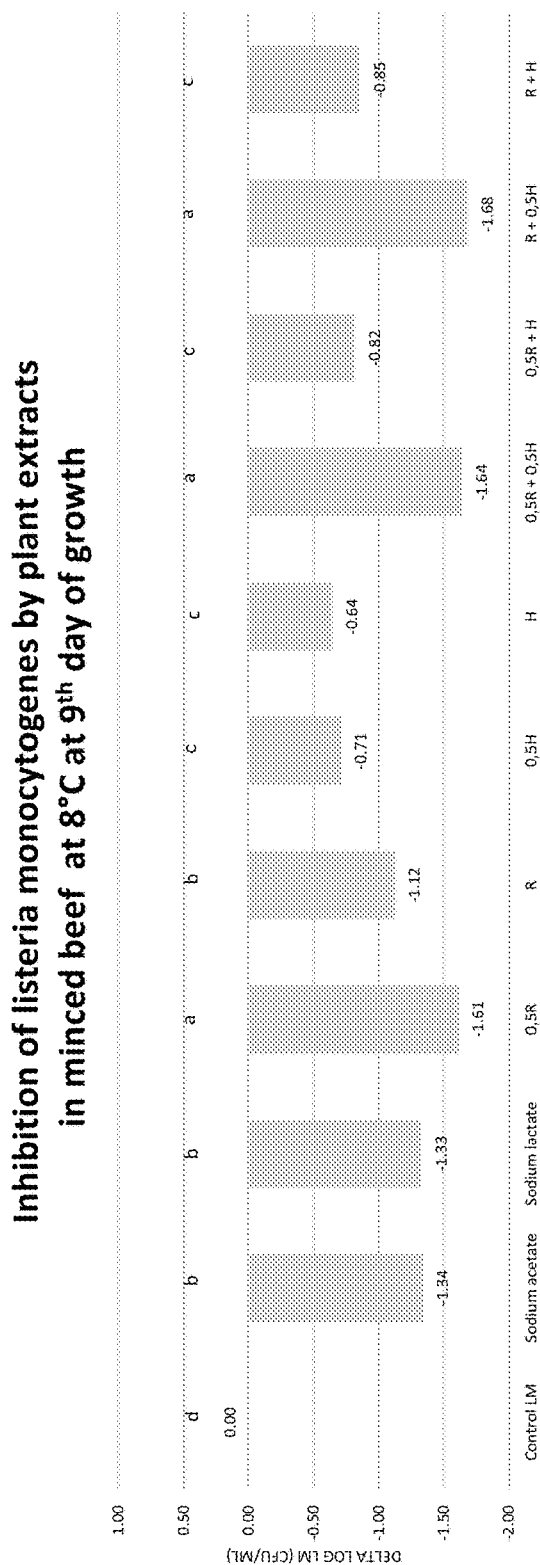
FIG. 8 is a graph showing inhibition of *Listeria monocytogenes* growth by plant extracts in minced beef at 8° C. at day 9.

Results of such testing at $6^{th}$ and $9^{th}$ day are presented in FIG. 7 and FIG. 8. Data are means of 2 to 6 replicates. Data represent log differences in L. monocytogenes growth in treated meat as compared to inoculated controls (non-treated meat). Data were statistically analyzed for significance at $p<0.05$ using ANOVA. Different letters indicate significant differences at $p<0.05$.

Results of such testing at $6^{th}$ day using rosemary extract and/or hesperidin are set forth in the following Table 1.

TABLE 1

| Rosemary extract (%) | Hesperidin (%) | Expected effect | Measured effect |
| --- | --- | --- | --- |
| R | 0 |  | −0.08 |
| 0 | H |  | −0.09 |
| R | H | −0.08 to −0.17 | 0.07* |

*Unexpected effect

Rosemary extract and/or hesperidin: full concentration effects on Listeria monocytogenes growth after 6 days of growth in meat: [(log(CFU/mL) in meat treated with plant extracts)−(log(CFU/mL) control meat (without treatment))]

It will be noted that at such short duration (6 days of growth in cold conditions), the difference in listerial growth in meat treated with plant extracts as compared with untreated meat, expressed in log, did not attain −0.5 log, which means that in such short time of growth, antilisterial effects could not be appreciated. It will be noted that at such short duration (6 days of growth in cold conditions), *Listeria monocytogenes* grew in control meat only by 0.29 log CFU/mL (FIG. 2).

It will be noted that when combined, the measured effect of the combination of rosemary extract and of hesperidin does not correspond to a synergistic effect at the above concentrations after 6 days of growth as the combinatory effect is unexpectedly antagonistic.

When concentrations were halved, the following expected effects calculated from the table above and measured effects were obtained and shown in Table 2.

TABLE 2

| Rosemary extract (%) | Hesperidin (%) | Expected effect | Measured effect |
|---|---|---|---|
| 0.5R | 0 | −0.04 | 0.04* |
| 0 | 0.5H | −0.045 | −0.37* |
| 0.5R | 0.5H | −0.045 to −0.085 | 0.11* |
| R | 0.5H | −0.045 to −0.125 | −0.07 |
| 0.5R | H | −0.04 to −0.13 | 0* |

*Unexpected effect

Rosemary extract and hesperidin: half concentrations and combinations of half and full concentrations effects on *Listeria monocytogenes* growth after 6 days of growth in meat:[(log(CFU/mL) in meat treated with plant extracts)−(log(CFU/mL) control meat (without treatment))]

It will be noted that at such short duration (6 days of growth in cold conditions), the difference in *listerial* growth in meat treated with plant extracts as compared with untreated meat, expressed in log, did not attain −0.5 log, which means that in such short time of growth, antilisterial effects could not be appreciated. It will be noted that at such short duration (6 days of growth in cold conditions), *Listeria monocytogenes* grew in control meat only by 0.29 log CFU/mL (FIG. 2).

It will be noted though, that, in the above Table 2, hesperidin applied at a half dose alone has surprisingly a greater antilisterial effect than at the full dose. Unexpected effect is signified by a star. On the other hand, effects of half dose of rosemary and of combination of half dose rosemary and full dose hesperidin were antagonistic from what was expected. Finally, effects of combination of half dose rosemary and half dose hesperidin and of combination of full dose rosemary and half dose hesperidin remained within additional range, as expected.

Results of such testing at 9$^{th}$ day using rosemary extract and/or hesperidin are set forth in the following Table 3.

TABLE 3

| Rosemary extract (%) | Hesperidin (%) | Expected effect | Measured effect |
|---|---|---|---|
| R | 0 | | −1.12 |
| 0 | H | | −0.64 |
| R | H | −1.76 | −0.85 |

*Unexpected effect

Rosemary extract and hesperidin: full concentration effects on *Listeria monocytogenes* after 9 days of growth in meat:[(log(CFU/mL) in meat treated with plant extracts)−(log(CFU/mL) control meat (without treatment))]

It will be noted that after 9 days of growth in cold conditions, the difference in *listerial* growth expressed in log CFU/mL exceeded −0.5 log CFU/mL, which means that antilisterial effects of all extracts and their concentrations and combinations presented in the above table could be appreciated within the commercially desirable period.

TABLE 4

| Rosemary extract (%) | Hesperidin (%) | Expected effect | Measured effect |
|---|---|---|---|
| 0.5R | 0 | −0.56 | −1.61* |
| 0 | 0.5H | −0.32 | −0.71* |
| 0.5R | 0.5H | −2.35 | −1.64 |
| R | 0.5H | −1.83 | −1.68 |
| 0.5R | H | −2.28 | −0.82 |

*Unexpected effect

Rosemary extract and hesperidin: half concentration and combinations of half and full concentrations effects on *Listeria monocytogenes* growth after 9 days of growth in meat:[(log(CFU/mL) in meat treated with plant extracts)−(log(CFU/mL) control meat (without treatment))]

After nine (9) days of growth in meat, extracts alone or their combinations at all tested concentrations inhibited the growth of *Listeria monocytogenes* by more than 0.5 log which means that they had an antilisterial effect in meat.

Figure 3:
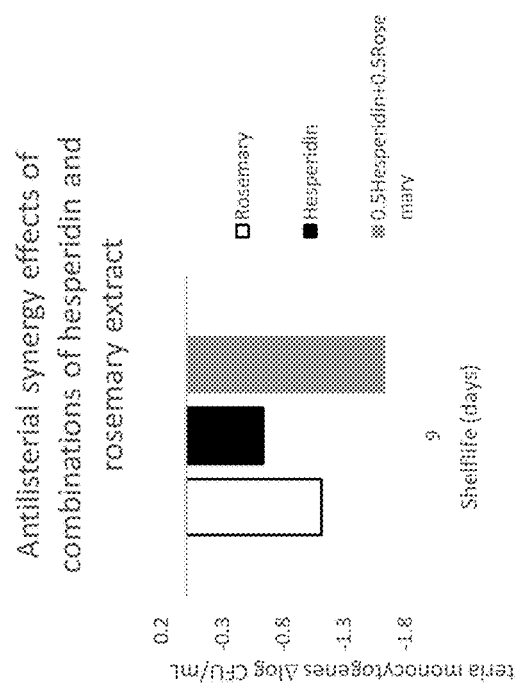
FIG. 3 is a graph showing antilisterial synergy effects of combinations of hesperidin and rosemary extract in accordance with the present invention.

Unexpectedly in view of the prior art, hesperidin had an antilisterial effect at all tested concentrations. Further, unexpectedly, rosemary extract or hesperidin alone had a greater antilisterial effect when used at half concentrations as compared to full concentrations. Still further, unexpectedly, rosemary extract combined with hesperidin at half concentrations had a greater antilisterial effect than each extract alone at full concentration. This is synergy (FIG. 3).

Figure 4:
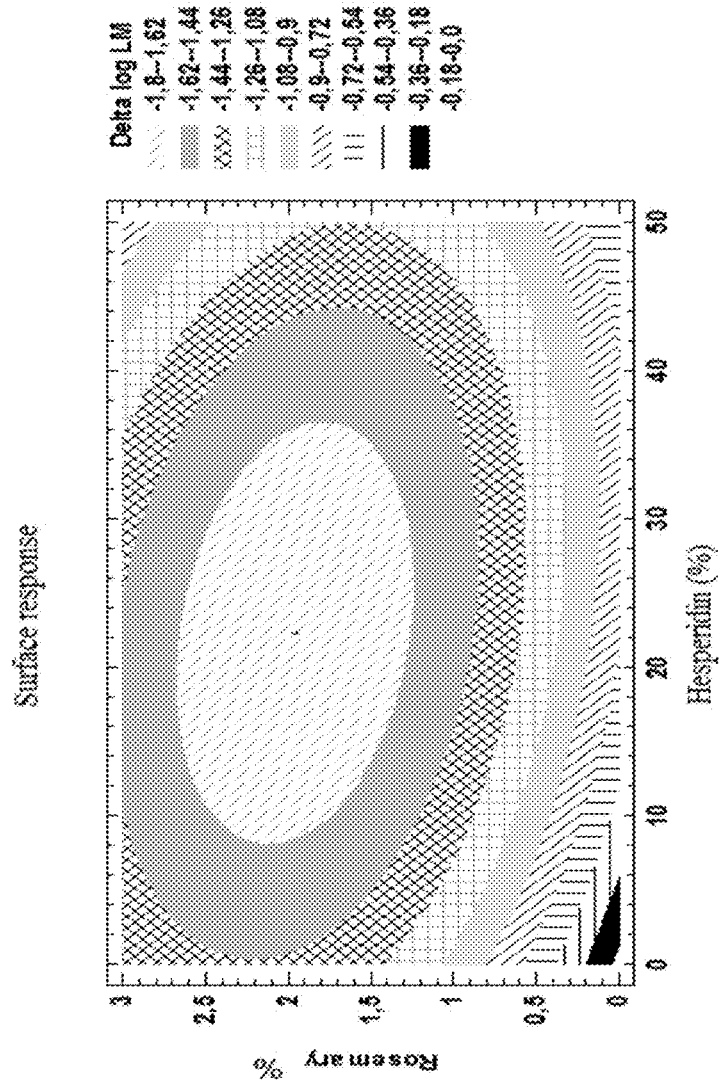
FIG. 4 is a graph showing antimicrobial surface response of different combinations of rosemary extract and hesperidin inhibiting and decreasing *Listeria monocytogenes* growth, in accordance with the present invention.

Different concentrations and their response surfaces were analyzed using surface response methodology factorial experimental design that was designed at three levels. These results are shown in FIG. 4. They indicate the following concentration ranges that provide antilisterial response in meat which is determined as: [(log(CFU/mL) in meat treated with plant extracts)−(log(CFU/mL) control meat (without treatment))]<0.5 as provided in Table 5.

TABLE 5

| Extract | Concentration (%) |
|---|---|
| Hesperidin | 0.5-48.0 |
| Rosemary extract | 0.2-3.0 |

Concentration ranges that provide antilisterial response in meat (%)

It will be noted that to insure antilisterial effect, any of the above extract concentrations (Table 5) can be added in combination or alone to the meat. The total percentage of the added extract, alone or in combination, to the meat did not exceed 1.18%.

During the *listerial* growth, color of meat was monitored and images were taken straight after addition of the extract (on the day 0) and on the 6$^{th}$ day of growth).

Each picture representing the "sample" at a different time scale was loaded in the open source image analysis program ImageJ. The software is commonly used in the food industry to measure different food parameters such as color or density (Reineke et al. 2011; Kelkar et al. 2011. In order to obtain representative values of the three color units red (R), green (G) and blue (B) of the RGB models, a line was drawn across the sample. The inbuilt RGB profile plot plugin was used to determine the different color values of each pixel along this line. The results are presented as variation of the different color value as a function of the pixel number along this line. The results were statistically analyzed for significant differences using ANOVA test at p<0.05. Per sample, more than 1000 pixels were analyzed.

Red Color of the Raw Meat

The color of the meat was appreciated by a panel of sensorial analysis. This panel distinguished the meat color between bright red, red, brown and green hues. All meat samples were bright red on the day 0 of experiments.

On the $6^{th}$ day, the overall panel appreciation described the color of different meat samples subjected to different meat treatments as following:

|  | Meat color at Day 6 |
| --- | --- |
| Control | brown |
| Sodium acetate | brown |
| Sodium lactate | brown |
| 0.5R | brown |
| R | red |
| 0.5H | green |
| H | brown |
| 0.5R + 0.5H | red |
| 0.5R + H | brown |
| R + 0.5H | red |
| R + H | brown |

During the *listerial* growth, color of meat supplemented or not with plant extracts was monitored and images were taken straight after addition of the extract (on the day 0) and on the $6^{th}$ day of growth).

Results of such monitoring at $6^{th}$ day using rosemary extract and hesperidin alone or in combination are set forth in the following Table 6:

TABLE 6

| Rosemary extract (%) | Hesperidin (%) | Expected effect | Measured effect |
| --- | --- | --- | --- |
| R | 0 |  | 11.05 |
| 0 | H |  | 10.69 |
| R | H | 21.75 | 15.39 |

Rosemary extract and hesperidin of full concentration effects on red meat color after 6 days of growth in meat. The effect was calculated using: [red color of meat with extract]−[red color of control meat (without extract)]

Contrary to the reports from the prior art, unexpectedly, Rosemary extract better preserved the red color of the meat as compared to the control. Hesperidin had slightly lower but similar effect.

The combination effect remains within the additional range and therefore was not found to be synergistic at these concentrations.

The combination of extracts as compared to the control significantly improves the preservation of the red color more than each extract alone.

TABLE 7

| Rosemary extract (%) | Hesperidin (%) | Expected effect | Measured effect |
| --- | --- | --- | --- |
| 0.5R | 0 | 5.53 | 14.143* |
| 0 | 0.5H | 5.35 | −1.63* |
| 0.5R | 0.5H | 12.51 | 17.16* |
| R | 0.5H | 9.42 | 15.03* |
| 0.5R | H | 16.22 | 13.33 |

*Unexpected effect

Rosemary extract and hesperidin at full and half concentrations and combinations of half and full concentrations effects on red meat color after 6 days of growth in meat. Each effect was calculated using: [red color of meat with extract]−[red color of control meat (without extract)]

Figure 5:
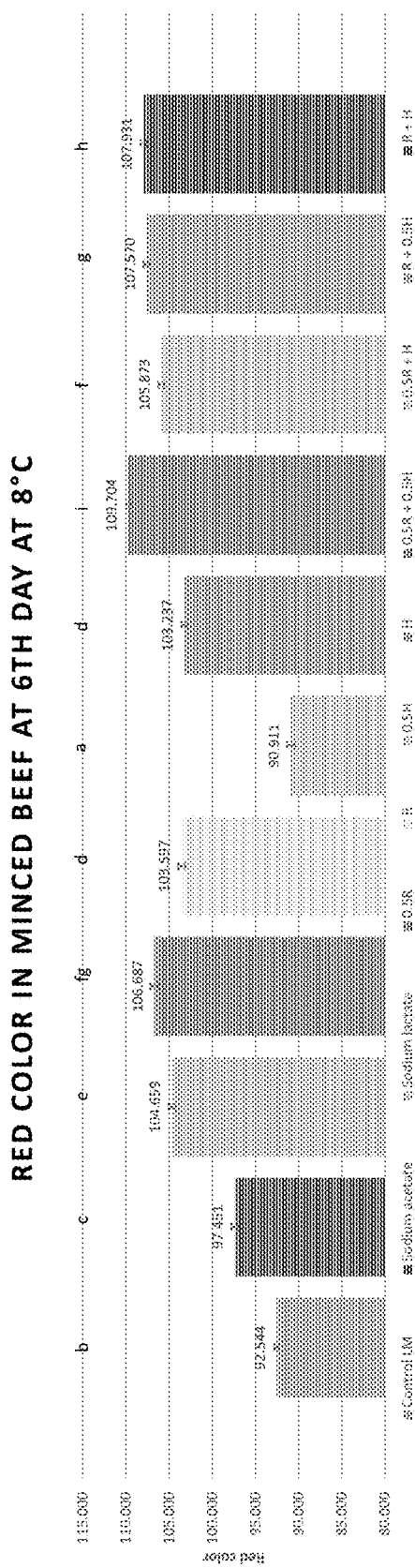
FIG. 5 is a bar chart showing red color values of the meat in accordance with the present invention with regard to combinations of rosemary extract and hesperidin in accordance with the present invention.

FIG. 5 shows that when the concentration in hesperidin added to meat is halved, it significantly decreased the preservation of the red color of meat as compared to the control.

Adding rosemary significantly improved the preservation of the meat color as compared to the untreated control meat. Unexpectedly, halving rosemary concentration provoked a greater effect in red color preservation of meat than the full rosemary concentration. In addition, unexpectedly, halving hesperidin concentration did not yield in a preservation effect of the red color as expected but at this concentration, hesperidin deteriorated the preservation of the red color as compared to the control. Further, unexpectedly, the effect on the preservation of the red color of the meat of the combination of full concentration of rosemary and of half concentration of hesperidin, exceeded the expected additional effects of rosemary at full concentration or of hesperidin at halved concentration alone. This is synergy.

Still further, unexpectedly, the effect on the preservation of the red color of the meat of the combination of half a concentration of rosemary and of half a concentration of hesperidin, exceeded the expected additional effects of half a concentration of rosemary or of hesperidin at halved concentration alone. This is synergy.

As to the rosemary extract at halved concentration and hesperidin at full concentration, their combination effect remained within the additional range and therefore was not found to be synergistic.

FIG. 5 shows that all combinations between rosemary and hesperidin at any here presented concentration significantly improved the preservation of the red color of the meat as compared to the control and as compared to typical antilisterial compounds such as sodium acetate and sodium lactate.

Mixtures of Rosemary and *Punica*

Growth of *Listeria monocytogenes* in Raw Meat

Figure 9:
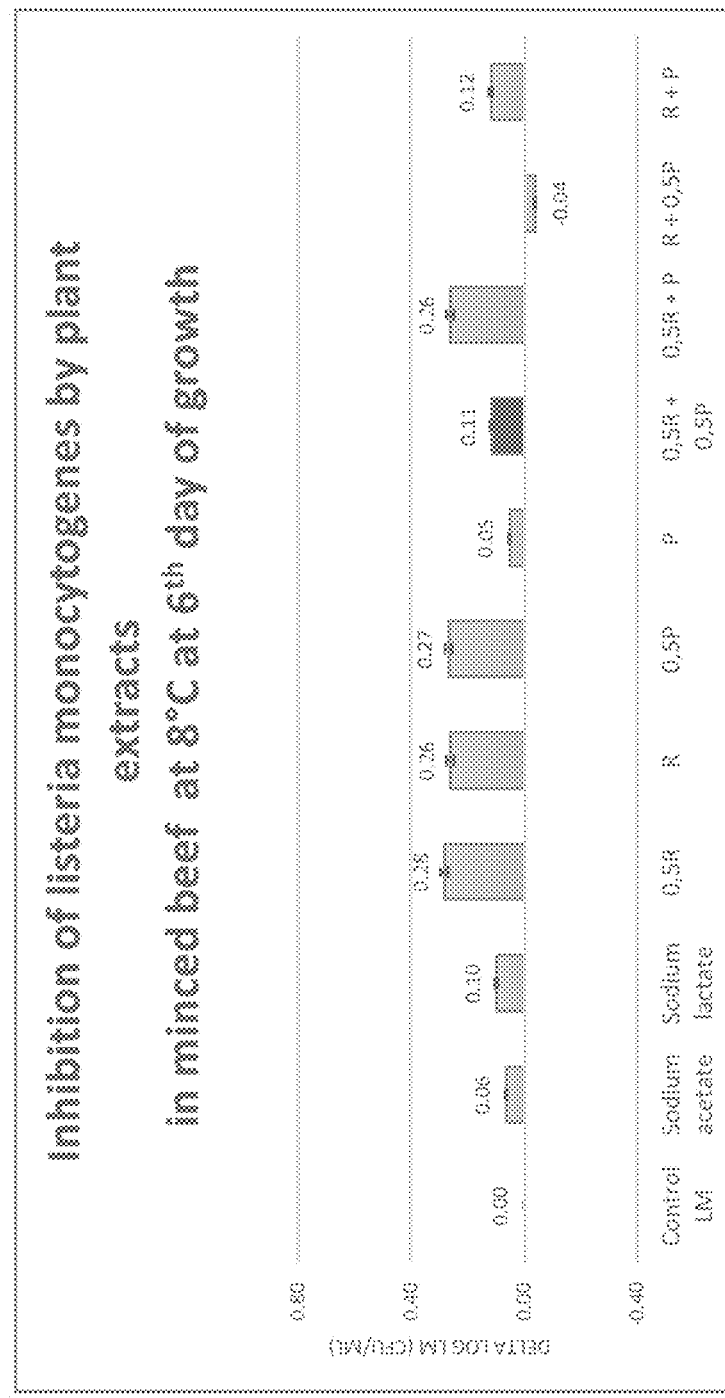
FIG. 9 is a chart showing inhibition of *Listeria monocytogenes* growth by plant extracts in minced beef at 8° C. at day 6.
Figure 10:
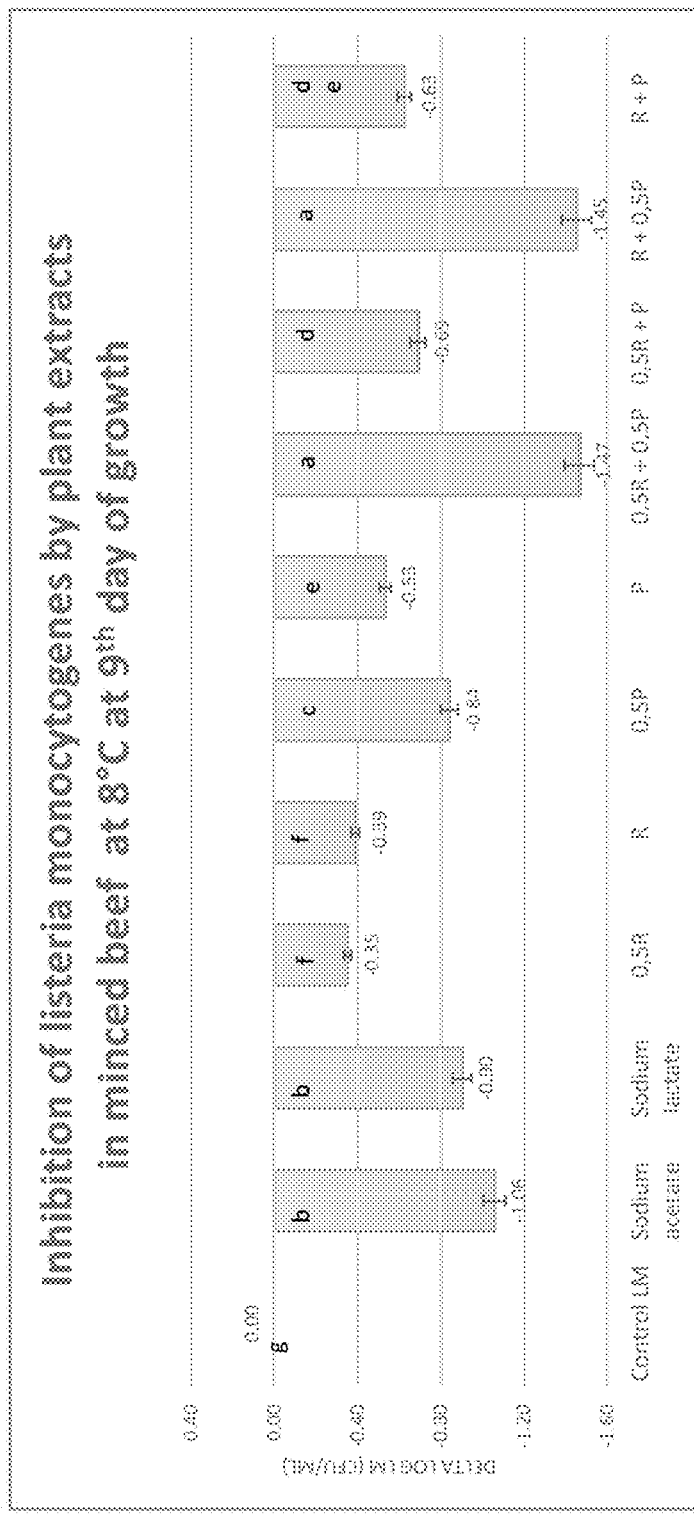
FIG. 10 is a chart showing inhibition of *Listeria monocytogenes* e by plant extracts in minced beef at 8° C. at day 9 in accordance with the present invention.

Results of such testing at $6^{th}$ and $9^{th}$ day are presented in FIG. 9 and FIG. 10. Data are means of 2 to 6 replicates. Data represent log differences in *L. monocytogenes* growth in treated meat as compared to inoculated controls (non-treated meat). Data were statistically analyzed for significance at p<0.05 using ANOVA. Different letters indicate significant differences at p<0.05.

TABLE 8

| Rosemary extract (%) | Punica extract (%) | Expected effect | Measured effect |
|---|---|---|---|
| R | 0 | | 0.26 |
| 0 | P | | 0.05 |
| R | P | 0.31 | 0.12* |

*Unexpected effect

Rosemary extract and/or Punica extract: full concentration effects on Listeria monocytogenes growth after 6 days of growth in meat: [(log(CFU/mL) in meat treated with plant extracts)−(log(CFU/mL) control meat (without treatment))]

It will be noted that at such short duration (6 days of growth in cold conditions), the difference in listerial growth in meat treated with plant extracts as compared with untreated meat, expressed in log, did not attain −0.5 log, which means that in such short time of growth, antilisterial effects could not be appreciated.

It will be noted that when combined, the measured effect of the combination of rosemary extract and of Punica extract did not correspond to a synergistic effect.

When concentrations were halved, the following expected effects calculated from the table above and measured effects were obtained:

TABLE 9

| Rosemary extract (%) | Punica extract (%) | Expected effect | Measured effect |
|---|---|---|---|
| 0.5R | 0 | 0.13 | 0.28 |
| 0 | 0.5P | 0.025 | 0.27 |
| 0.5R | 0.5P | 0.55 | 0.11* |
| R | 0.5P | 0.53 | −0.03* |
| 0.5R | P | 0.33 | 0.26* |

*Unexpected effect

Rosemary extract and/or Punica extract: half concentrations and combinations of half and full concentrations effects on Listeria monocytogenes growth after 6 days of growth in meat: [(log(CFU/mL) in meat treated with plant extracts)−(log(CFU/mL) control meat (without treatment))]

It will be noted that at such short duration (6 days of growth in cold conditions), the difference in listerial growth expressed in log did not attain −0.5 log, which means that in such short time of growth, antilisterial effects could not be appreciated.

Unexpected Effect is Signified by a Star

Unexpectedly, the antilisterial effect of the combination of half a concentration of rosemary and of half concentration of Punica, exceeded the expected additional effects of rosemary at halved concentration or of Punica at halved concentration, alone. This is synergy.

Further, unexpectedly, the antilisterial effect of the combination of full concentration of rosemary and of half concentration of Punica, exceeded the expected additional effects of rosemary at full concentration or of Punica at halved concentration, alone. This is synergy.

Still further, unexpectedly, the antilisterial effect of the combination of half a concentration of rosemary and of full concentration of Punica, exceeded the expected additional effects of rosemary at halved concentration or of Punica at full concentration, alone. This is synergy.

Results of such testing at 9$^{th}$ day using rosemary extract and/or Punica extract are set forth in Table 10.

TABLE 10

| Rosemary extract (%) | Punica extract (%) | Expected effect | Measured effect |
|---|---|---|---|
| R | 0 | | −0.39 |
| 0 | P | | −0.53 |
| R | P | −0.92 | −0.63 |

*Unexpected effect

Rosemary extract and Punica extract: full concentration effects on Listeria monocytogenes growth after 9 days of growth in meat: [(log(CFU/mL) in meat treated with plant extracts)−(log(CFU/mL) control meat (without treatment))]

As mentioned above, in microbiology, it will be noted that a treatment has an antibacterial effect if its effect exceeds −0.5 log CFU/mL as compared to the untreated control. It will be noted that after nine (9) days of growth in cold conditions, compared to the control, the difference in listerial growth expressed in log CFU/mL exceeded −0.5 log CFU/mL when the meat was treated with full concentrations of Punica or of the combination of full concentration of rosemary and of full concentration of Punica. Rosemary alone at the full concentration did not significantly inhibit the listerial growth as compared to the untreated control meat. However, combining rosemary at full concentration with Punica at full concentration had a greater antilisterial effect than when extracts were used alone and enabled to exceed the threshold of −0.5 log CFU/mL that is required for a significant effect in antilisterial growth.

TABLE 11

| Rosemary extract (%) | Punica extract (%) | Expected effect | Measured effect |
|---|---|---|---|
| 0.5R | 0 | −0.195 | −0.35* |
| 0 | 0.5P | −0.265 | −0.84* |
| 0.5R | 0.5P | −1.19 | −1.47* |
| R | 0.5P | −1.23 | −1.45* |
| 0.5R | P | −0.88 | −0.69 |

*Unexpected effect

Rosemary extract and Punica extract: half concentrations and combinations of half and full concentrations effects on Listeria monocytogenes growth after 9 days of growth in meat: [(log(CFU/mL) in meat treated with plant extracts)−(log(CFU/mL) control meat (without treatment))]

After 9 days of growth in meat, all but one extracts alone or their combinations at almost all tested concentrations inhibited the growth of Listeria monocytogenes by more than 0.5 log CFU/mL as compared to the control which means that they had an antilisterial effect in meat. Only rosemary extract alone when tested at half a concentration did not attain the difference of −0.5 log CFU/mL as compared to the control.

Unexpectedly, Punica extract alone had a greater antilisterial effect when used at half concentration as compared to a full concentration. Further, unexpectedly, when used at a half concentration, rosemary extract had a greater antilisterial effect than expected. Still further, unexpectedly, the antilisterial effect of the combination of half concentration of rosemary and of half concentration of Punica extract, exceeded their expected additional effects of rosemary at halved concentration or of Punica extract at halved concentration alone. This is synergy.

In addition, unexpectedly, the antilisterial effect of the combination of full concentration of rosemary and of half concentration of *Punica* extract, exceeded the expected additional effects of rosemary at full concentration or of hesperidin at halved concentration, alone. This is synergy.

Further, unexpectedly, rosemary extract combined with *Punica* extract at half concentrations had a greater antilisterial effect than each extract alone at full concentration. This is synergy (See e.g., FIG. 1).

Figure 11:
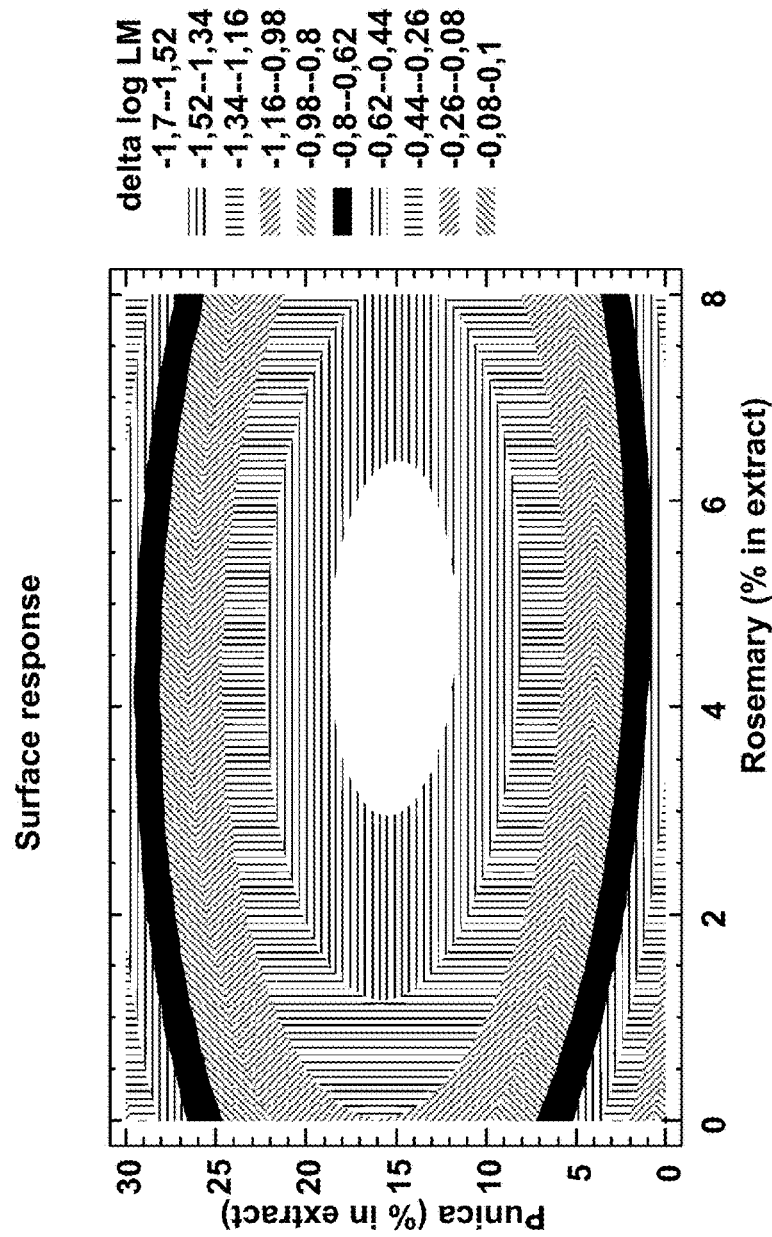
FIG. 11 is a graph showing in accordance with the present invention, antimicrobial surface response of different combinations of rosemary and *punica* extract inhibiting and decreasing *Listeria monocytogenes* growth.

Different concentrations and their response surfaces were analyzed using surface response methodology factorial experimental design that was designed at three levels. These results are shown in FIG. 11. They indicate the following concentration ranges that provide antilisterial response in meat which is determined as [log(CFU/mL) in meat treated with plant extracts]–[log(CFU/mL) control meat (without plant extract)]<–1 as shown in Table 12.

TABLE 12

| Extract | Extract (%) |
|---|---|
| Punica extract | 5.0-24.0 |
| Rosemary extract | 0.5-8.0 |

* Extract %

It will be noted that to insure antilisterial effect, any of the above extract concentrations (Table 12) can be added in combination or alone to the meat. The total percentage of the added extract, alone or in combination, to the meat did not exceed 0.18%.

Red Color of the Raw Meat

The color of the meat was appreciated by a panel of sensorial analysis. This panel distinguished the meat color between bright red, red, brown and green hues. All meat samples were bright red on the day 0 of experiments.

On the $6^{th}$ day, the overall panel appreciation described the color of different meat samples subjected to different meat treatments as following:

| | Meat color at Day 6 |
|---|---|
| Control | brown |
| Sodium acetate | brown |
| Sodium lactate | brown |
| 0.5R | brown |
| R | brown |
| 0.5P | red |
| P | red |
| 0.5R + 0.5P | red |
| 0.5R + P | brown |
| R + 0.5P | red |
| R + P | brown |

During the *listerial* growth, color of meat supplemented or not with plant extracts was monitored and images were taken straight after addition of the extract (on the day 0) and on the $6^{th}$ day of growth). Red pixels were quantified as explained above in the Methods section.

Results of such monitoring at $6^{th}$ day using rosemary extract and *Punica* extract alone or in combination are set forth in the following:

TABLE 13

| Rosemary extract (%) | Punica extract (%) | Expected effect | Measured effect |
|---|---|---|---|
| R | 0 | | –3.72 |
| 0 | P | | –5.60 |
| R | P | –9.32 | 1.27* |

*Unexpected effect

Rosemary extract and *Punica* extract: full concentration effects on the preservation of the red color of meat after 6 days of growth in meat. The effect was calculated by: [red color of meat with extract]–[red color of control meat (without extract)]

At the above concentrations (Table 13), when added alone, rosemary or *Punica* extract deteriorated the preservation of the red color of the meat as compared to the control. It was therefore expected that when combined, these extracts would even further deteriorate the preservation of the red color of the meat. Unexpectedly, when combined, rosemary and *Punica* extracts improved the preservation of the red color of the meat as compared to the control.

Unexpectedly, the effect on the preservation of the red color of the meat of the combination of full concentration of rosemary and of full concentration of *Punica*, exceeded the expected additional effects of rosemary at full concentration or of full concentration of *Punica* alone. This is synergy.

TABLE 14

| Rosemary extract (%) | Punica extract (%) | Expected effect | Measured effect |
|---|---|---|---|
| 0.5R | 0 | –1.86 | 1.07* |
| 0 | 0.5P | –2.80 | –0.34* |
| 0.5R | 0.5P | 0.73 | 4.45* |
| R | 0.5P | –4.04 | –2.71* |
| 0.5R | P | –4.53 | 6.37* |

*Unexpected effect

Rosemary extract and *Punica* extract: full and half concentrations and combinations of half and full concentrations effects on the preservation of the red color of the meat after 6 days of *Listerial* growth in meat. Each effect was calculated by: [red color of meat with extract]–[red color of control meat (without extract)]

As full concentrations of rosemary and of *Punica* extracts deteriorated the preservation of the red color of the meat, it was expected that halved concentrations would have also deteriorated the preservation of the red color of the meat. Unexpectedly, halving the added rosemary concentration significantly improved the preservation of the red color of the meat as compared to the untreated control.

Adding rosemary significantly improved the preservation of the meat color as compared to the untreated control meat. Unexpectedly, halving the concentration of the added *Punica* extract did not deteriorate as much as expected the preservation of the red color of the meat.

Further, unexpectedly, the improvement of the preservation of the red color of the combination of half concentration of rosemary and of half concentration of *Punica* extract, exceeded their expected additional effects of rosemary at halved concentration or of *Punica* extract at halved concentration alone. This is synergy.

In addition, unexpectedly, the improvement of the preservation of the red color of the combination of full concentration of rosemary and of half concentration of *Punica* extract, exceeded the expected additional effects of rosemary at full concentration or of hesperidin at halved concentration, alone. This is synergy.

Still further, unexpectedly, the improvement of the preservation of the red color of the combination of full concentration of *Punica* extract and of half concentration of rosemary extract, exceeded the expected additional effects of *Punica* extract at full concentration or of rosemary extract at halved concentration, alone. This is synergy.

Unexpectedly, the combination of full concentration of *Punica* extract and of half concentration of rosemary extract improved the preservation of the color of the meat whereas it was expected that the preservation of the color be deteriorated upon application of such combination.

Figure 6:
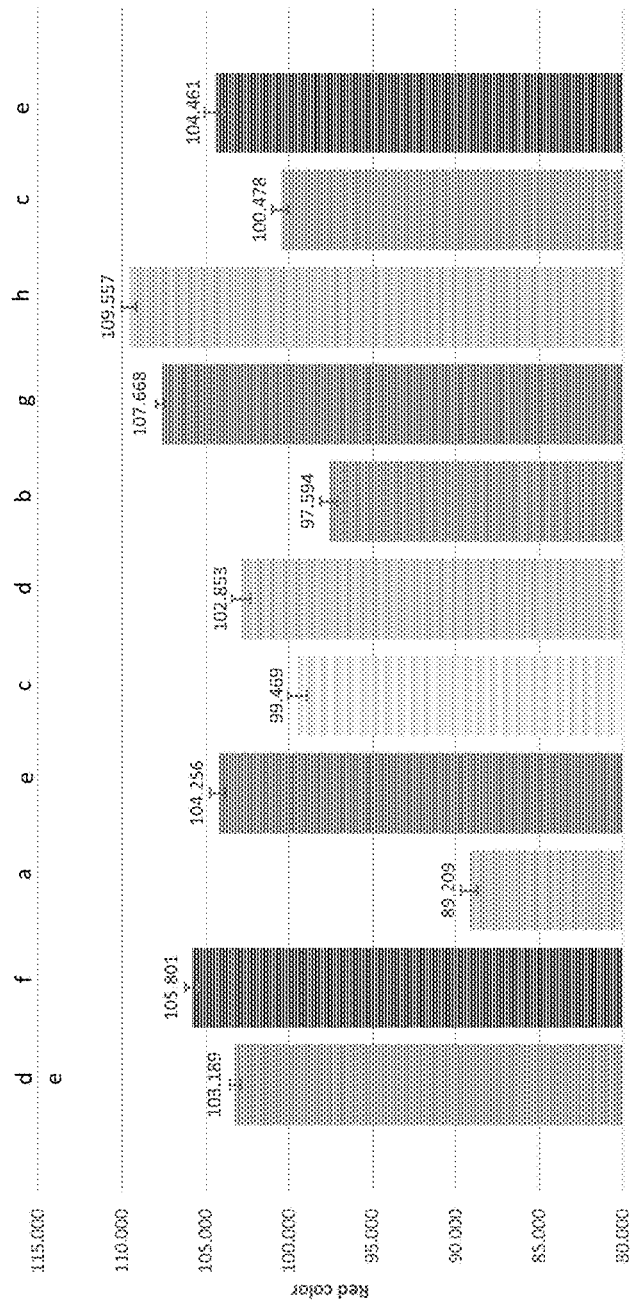
FIG. 6 is a bar chart showing red color values of meat in accordance with the present invention with regard to various combinations of rosemary and *punica* extract in accordance with the present invention.

FIG. 6 shows that all combinations between rosemary and *Punica* extract at any here presented concentration significantly improved the preservation of the red color of the meat as compared to the control and as compared to classic antilisterial agents such as Sodium acetate and Sodium lactate.

One of ordinary skill in the art will recognize that additional embodiments are also possible without departing from the teachings of the presently-disclosed subject matter. This detailed description, and particularly the specific details of the exemplary embodiments disclosed herein, is given primarily for clarity of understanding, and no unnecessary limitations are to be understood therefrom, for modifications will become apparent to those skilled in the art upon reading this disclosure and can be made without departing from the spirit and scope of the presently-disclosed subject matter.

REFERENCES

Numerous references have been cited throughout this disclosure. All references cited in this disclosure including the three listed both are incorporated by reference.

Kai Reineke, Henning Weich, Dietrich Knorr, "The Influence of Sugars on Pressure Induced Starch Gelatinization", Procedia Food Science, Vol. 1, (2011), pages 2040-2046.

Shivangi Kelkar, Scott Stella, Carol Boushey, Martin Okos, "Developing novel 3D measurement techniques and prediction method for food density determination", Procedia Food Science, Vol. 1, (2011), pages 483-491.

S. Chaillou, S. Christieans, M. Rivollier, I. Lucquin, M. G. Champomier-Vergès, M. Zagorec; "Quantification and efficiency of Lactobacillus sakei strain mixtures used as protective cultures in ground beef"; Meat Science 97, (3) (2014), pages 332-338.

The invention claimed is:

1. A composition comprising a *Punica* extract and a rosemary extract, wherein a majority of the volatile oil components have been removed from the rosemary extract, and the rosemary extract contains a rosemary phenolic diterpene selected from carnosic acid and carnosol and mixtures thereof, and wherein the composition comprises 13.5 to 27% by weight *Punica* extract and 3.33 to 6.65% by weight rosemary extract.

2. The composition according to claim 1, further comprises a carrier selected from arabic gum, dextrose, salt, mono & diglycerides of fatty acids, MPG, Polysorbate 80, dextrose, vegetable oil, glucose syrup, glycerin, decaglycerol monooleate, fatty acid esters, benzyl alcohol, ethyl alcohol, propylene, glycol, polysorbates, sorbitans, sorbitan trioleate, capric/caprylic triglycerides, and combinations thereof.

3. The composition according to claim 1, further comprises a carrier of maltodextrin having a structure distinct from a starch from which the maltodextrin originates.

4. The composition according to claim 2, wherein the composition is in the form of a dry powder.

5. The composition according to claim 2, further comprises one or more flavorings and adjuvants.

6. The composition according to claim 2, wherein the composition is in liquid form.

7. A food product comprising a food and the composition of claim 1.

8. The food product of claim 7, wherein the food is selected from the group consisting of meat, poultry and fish.

9. The food product of claim 8, wherein the meat, poultry and fish are fresh meat, poultry and fish.

10. The food product according to claim 7, wherein the rosemary extract containing rosemary phenolic diterpene in an amount of 12 ppm or more of rosemary phenolic diterpene selected from carnosic acid, carnosol, and mixtures thereof, and 56 ppm or more of ellagic acid and 19 ppm or more of punicalagins from *Punica* extract.

11. The food product according to claim 10, containing between 12 and 188 ppm of rosemary phenolic diterpene and between 4 and 24 ppm ellagic acid and between 19 and 120 ppm of punicalagins *Punica* extract.

12. The food product according to claim 7, containing between 12 and 188 ppm of rosemary phenolic diterpene and between 4 and 24 ppm of ellagic acid and between 19 and 120 ppm of punicalagins *Punica* extract.

13. A packaged food product comprising a food according to claim 7, wherein the food is packaged in an atmosphere comprising 20% or more oxygen.

14. A packaged food product comprising a food according to claim 7, wherein the food is packaged in an atmospheric environment.

15. A method for processing food comprising:
applying to or incorporating into a food, a composition comprising *Punica* extract and a rosemary extract, wherein a majority of the volatile oil components have been removed from the rosemary extract, and the rosemary extract contains a rosemary phenolic diterpene selected from carnosic acid and carnosol and mixtures thereof, wherein the composition comprises 13.5 to 27% by weight *Punica* extract and 3.33 to 6.65% by weight rosemary extract.

16. The method of claim 15, further comprising packaging the food in an atmosphere that contains 20% or more oxygen.

17. The method of claim 15, wherein the food is selected from the group consisting of fresh meat, fish or poultry.

18. The method according to claim 15, wherein applying to or incorporating into food comprises applying the composition, in the form a dry powder, to the food.

19. The method according to claim 15, wherein applying to or incorporating into food comprises applying a single composition comprising both the rosemary extract and *Punica* extract to or incorporate into the food.

20. A food product comprising a food in combination with rosemary extract essentially free of native essential oil which contains a rosemary phenolic diterpene selected from carnosic acid, and carnosol, and mixtures thereof, and *Punica* extract, wherein the food product comprises a composition comprising 13.5 to 27% by weight *Punica* extract and 3.33 to 6.65% by weight rosemary extract, and wherein *Punica* ellagic acid of the *Punica* extract is present in the food in an amount between 4 and 24 ppm and where *Punica* punicalagins are present in an amount between 19 and 120 ppm.

21. The food product of claim 20, wherein the food is selected from the group consisting of meat, poultry and fish.

22. The food product according to claim 20, containing between 12 and 188 ppm of rosemary phenolic diterpene and between 4 and 24 ppm ellagic acid of *Punica* extract and between 19 and 120 ppm punicalagins of *Punica* extract.

23. The food product according to claim 20, wherein the rosemary extract and *Punica* extract are in the form of a composition which additionally contains a carrier selected from the group consisting of arabic gum, dextrose, salt, mono & diglycerides of fatty acids, MPG, Polysorbate 80, dextrose, vegetable oil, glucose syrup, glycerin, decaglycerol monooleate, fatty acid esters, benzyl alcohol, ethyl alcohol, propylene, glycol, polysorbates, sorbitans, sorbitan trioleate, capric/caprylic triglycerides, dextrose and combinations thereof.

24. The food product according to claim 23, wherein the composition is in a dry form.

25. The food product according to claim 23, wherein the composition is in a liquid form.

26. A method for preparing a food product, comprising: applying to or incorporating into food, a combination of a rosemary extract which is essentially free of native essential oil and is antimicrobial and which contains a rosemary phenolic diterpene selected from carnosic acid, and carnosol, and mixtures thereof, and *Punica* extract, wherein the combination of rosemary extract essentially free of native essential oil and *Punica* extract comprises 13.5 to 27% by weight *Punica* and 3.33 to 6.65% by weight, and wherein *Punica* extract is present in the food in an amount between 4 and 24 ppm ellagic acid of *Punica* extract and between 19 and 120 ppm punicalagins of *Punica* extract.

27. The method of claim 26, wherein the food is meat, fish or poultry.

28. The method of claim 27, wherein the meat, fish or poultry is fresh meat, fish or poultry.

29. The method of claim 26, wherein the method extends the color life, inhibits, decreases and/or limits bacterial growth in the food product.

30. The method claim 29, wherein the bacterial growth inhibited, decreases and/or limited is *listeria*.

31. The composition of claim 1, wherein the *Punica* extract is selected from the group consisting of punicalagins and ellagic acid.

* * * * *